(12) United States Patent
Sterk

(10) Patent No.: US 6,933,296 B2
(45) Date of Patent: Aug. 23, 2005

(54) COMPOUNDS EFFECTIVE AS β2-ADRENORECEPTOR AGONISTS AS WELL AS PDE4-INHIBITORS

(75) Inventor: Geert Jan Sterk, Utrecht (NL)

(73) Assignee: Altana Pharma B.V., Zwanenburg (NL)

( * ) Notice: Subject to any disclaimer, the term of this patent is extended or adjusted under 35 U.S.C. 154(b) by 48 days.

(21) Appl. No.: 10/296,411

(22) PCT Filed: Jun. 1, 2001

(86) PCT No.: PCT/EP01/06230

§ 371 (c)(1),
(2), (4) Date: Apr. 2, 2003

(87) PCT Pub. No.: WO01/94319

PCT Pub. Date: Dec. 13, 2001

(65) Prior Publication Data

US 2003/0195215 A1 Oct. 16, 2003

(30) Foreign Application Priority Data

Jun. 5, 2000 (EP) .......................................... 00111795

(51) Int. Cl.[7] ..................... C07D 237/04; C07D 407/12; A61K 31/50; A61K 31/501; A61P 11/06

(52) U.S. Cl. .................. 514/247; 514/248; 514/252.04; 544/230; 544/237; 544/238; 544/239

(58) Field of Search ................................ 514/247, 248, 514/252.04; 544/230, 237, 238, 239

(56) References Cited

FOREIGN PATENT DOCUMENTS

| | | |
|---|---|---|
| EP | 0 030 835 | 6/1981 |
| EP | 0 763 534 | 3/1997 |
| EP | 0 934 933 | 8/1999 |
| JP | 58146571 | 9/1983 |
| PL | 164079 | 6/1994 |
| WO | 94/12461 | 6/1994 |
| WO | 98/31674 | 7/1998 |
| WO | 98/37894 | 9/1998 |
| WO | 99/31071 | 6/1999 |
| WO | 99/31090 | 6/1999 |
| WO | 00/12078 | 3/2000 |

OTHER PUBLICATIONS

Shire, M.G. et al, Exp. Opin. Ther. Patents, 8, 1998, 531–544.*
He, W. et al, J. Med. Chem., 41, 1998, 4216–4223.*
Duplantier, A.J. et al, J. Med. Chem., May, 1998, vol. 41, No. 13, pp. 2268–2277.*
Doherty, A.M., Current Opinion Chemical Biology, 1999, 3, 466–473.*
West, Anthony R., Solid State Chemistry and its Application, Wiley, New York, 1988, pp. 358 & 365.*
Giembycz, M.A.Drugs Feb. 2000, vol. 59, No. 2, pp. 193–212.*
David J.W. Grant, "University of Minnesota—Twin Cities Campus College of Pharmacy, Annual Report", [online] 1999, [retrieved on Feb. 13, 2003]. Retrieved from the internet, <http://www.msi.umn.edu/general/Reports/ar99/departments/pharmacy.html>.*
Burnouf, et al. "Chapter 10: Phosphodiesterases 4 Inhibitors", Section II—Cardiovascular and Pulmonary Diseases, *Annual Reports* in Medicinal Chemistry, 33 (1998) pp. 91–101.
Souness, et al. "Immunosuppressive and anti–inflammatory effects of cyclic AMP phosphodiesterase (PDE) type 4 inhibitors", Immunopharmacology, 47, (2000), pp. 127–162.
Dyke, et al., "The therapeutic potential of PDE4 inhibitors", *Exp. Opin. Invest. Drugs* (1999) 8(9): 1301–1325.
Norman, Peter, "PDE4 Inhibitors 1999", *Exp. Opin. Ther. Patents*, (1999) 9 (8) :1101–1118.

* cited by examiner

Primary Examiner—Thomas C. McKenzie
(74) Attorney, Agent, or Firm—Nath & Associates PLLC; Joshua B. Goldberg; Sheldon M. McGee

(57) ABSTRACT

The compounds of formula I in which $Ar_1$, A, R6, R7, R8 and $Ar_2$ have the meanings as given in the description are novel effective bronchial therapeutics

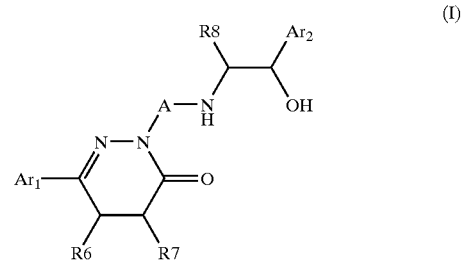

9 Claims, No Drawings

COMPOUNDS EFFECTIVE AS β2-ADRENORECEPTOR AGONISTS AS WELL AS PDE4-INHIBITORS

FIELD OF APPLICATION OF THE INVENTION

The invention relates to novel compounds, which act simultaneously as β2-adrenoreceptor agonist and as PDE4-inhibitor. They are used in the pharmaceutical industry for the production of medicaments.

KNOWN TECHNICAL BACKGROUND

International Patent Applications WO98/31674, WO99/31071 and WO99131090 disclose phthalazinone derivatives having selective PDE4 inhibitory properties. In the International Patent Application WO94/12461 and in the European Patent Application EP 0 763 534 3-aryl-pyridazin-6-one respectively arylalkyl-diazinone derivatives are described as selective PDE4 inhibitors.

In the International Patent Application WO98/37894 the combined application of PDE-inhibitors with adenylat-cyclase-agonists is described. In this context β-sympathomimetics are mentioned as one possible example of an adenylat-cyclase-agonist.

In the International Patent Application WO00/12078 is disclosed the combined application of a PDE4 inhibitor with a beta adrergenic bronchodilator for the treatment of asthma and COPD.

DESCRIPTION OF THE INVENTION

It has now been found that the pyridazinones, which are described in greater details below, have surprising and particularly advantageous properties.

The invention thus relates to compounds of the formula I:

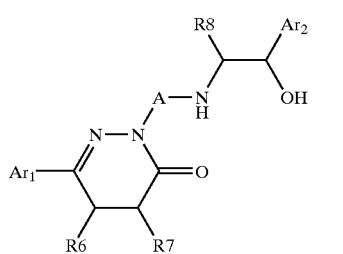

(I)

in which $Ar_1$ represents a phenyl radical of formula (Ia) substituted by R1 and R2 or a dihydrobenzofuranyl radical of formula (Ib) substituted by R3, R4 and R5:

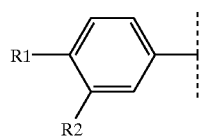

(Ia)

-continued

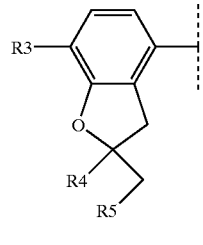

(Ib)

wherein
R1 is hydroxyl, halogen, 1–4C-alkoxy or 1–4C-alkoxy which is completely or predominantly substituted by fluorine,
R2 is hydroxyl, halogen, 1–8C-alkoxy, 3–7C-cycloalkoxy, 3–7C-cycloalkylmethoxy, or 1–4C-alkoxy which is completely or predominantly substituted by fluorine,
R3 is 1–4C-alkoxy, 3–5C-cycloalkoxy, 3–5C-cycloalkylmethoxy, or 1–4C-alkoxy which is compompletely or predominantly substituted by fluorine,
R4 is 1–4C-alkyl and
R5 is hydrogen or 1–4C-alkyl,
or wherein
R4 and R5 together and with inclusion of the two carbon atoms, to which they are bonded, form a spiro-linked 5-, 6- or 7-membered hydrocarbon ring, optionally interrupted by an oxygen or sulphur atom,
R6 and R7 represent independently from one another hydrogen or 1–4C-alkyl, or R6 and R7 together and with inclusion of the two carbon atoms, to which they are bonded, form a group selected from:

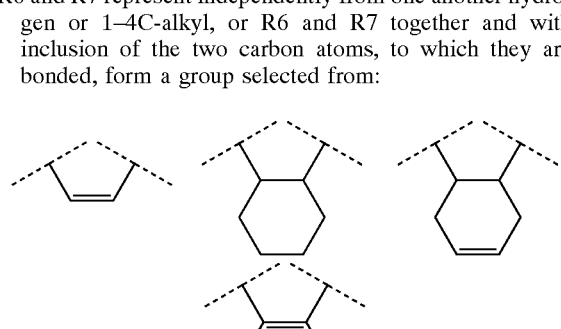

A represents —$C_mH_{2m}$—Y—X—$C_nH_{2n}$— or —Y—X—$C_mH_{2m}$—Z—$C_nH_{2n}$—, wherein
X represents a bond, —O—(oxygen), —S—(sulfur), —NH—, —C(O)—, —S(O)$_2$—, —C(O)—NH—, —NH—C(O)—, —C(S)—NH—, —NH—C(S)—, —NH—C(O)—NH— or —NH—C(S)—NH—,
Y represents a bond, phenylene, 4–8C-cycloalkylene or azacycloalkylene,
Z represents —O—, —S—, —S(O)$_2$—, —NH—C(O)—, —C(O)—NH—, —NH—C(S)— or —C(S)—NH—,
m is an integer from 0 to 4,
n is an integer from 1 to 4,
R8 is hydrogen or 1–4C-alkyl,
$Ar_2$ represents a 8-hydroxy-1H-quinolin-2-on-5-yl radical or a phenyl radical substituted by R9, R10 and R11,
wherein
R9 is hydrogen, halogen, hydroxyl, amino, ureido [—NH—C(O)—NH$_2$], formylamino [—NH—C(O)H], 1–4C-alkylcarbonylamino, di-1–4C-alkylaminocarbonyloxy, tolylcarbonyloxy [—O—C(O)—$C_6H_4$—$CH_3$], hydroxymethyl, 1–4C-alkylcarbonyloxy, 1–4C-alkyl, 1–4C-alkoxy, 1–4C-alkylsulfonylamino, 1–4C-alkylsulfonylmethyl or 1–4C-alkoxy-1–4C-alkyl, R10 is hydrogen, halogen, hydroxyl, cyano, trifluoromethyl, tolylcarbonyloxy [—O—C(O)—C$_6$H$_4$—CH$_3$], hydroxymethyl or 1–4C-alkylcarbonyloxy, R11 is hydrogen or halogen, and the salts of these compounds.

1–4C-alkyl is a straight-chain or branched alkyl radical having 1 to 4 carbon atoms. Examples are the butyl, isobutyl, sec-butyl, tert-butyl, propyl, isopropyl, ethyl and methyl radicals.

Halogen within the meaning of the invention is chlorine, bromine or fluorine.

1–4C-alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, ethoxy and methoxy radicals.

3–7C-cycloalkoxy stands for cyclopropyloxy, cyclobutyloxy, cyclopentyloxy, cyclohexyloxy and cycloheptyloxy.

3–7C-cycloalkylmethoxy stands for cyclopropylmethoxy, cyclobutylmethoxy, cyclopentylmethoxy, cyclohexylmethoxy and cycloheptylmethoxy.

1–4C-alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1–4C-alkoxy group are replaced by fluorine atoms.

As spiro-linked 5-, 6- or 7-membered hydrocarbon rings, optionally interrupted by an oxygen or sulphur atom, may be mentioned the cyclopentane, cyclohexane, cycloheptane, tetrahydrofuran, tetrahydropyran and the tetrahydrothiophen ring.

Possible radicals —(CH$_2$)$_m$—, in which m can have the meaning 0, 1, 2, 3 or 4 are straight chain or branched divalent alkylene radicals. Examples which may be mentioned are the butylene, isobutylene, sec-butylene, tert-butylene, propylene, isopropylene, ethylene and the methylene radical. The radical —(CH$_2$)$_m$— represents a bond, if m is zero.

Possible radicals —C$_m$H$_{2m}$—, in which m can have the meaning 0, 1, 2, 3 or 4 are straight chain or branched divalent alkylene radicals. Examples which may be mentioned are the butylene, isobutylene, sec-butylene, tert-butylene, propylene, isopropylene, ethylene and the methylene radical. The radical —C$_m$H$_{2m}$— represents a bond, if m is zero.

Possible radicals —(CH$_2$)$_n$—, in which n can have the meaning 1, 2, 3 or 4 are straight chain or branched divalent alkylene radicals. Examples which may be mentioned are the butylene, isobutylene, sec-butylene, tert-butylene, propylene, isopropylene, ethylene and the methylene radical.

Possible radicals —C$_n$H$_{2n}$—, in which n can have the meaning 1, 2, 3 or 4 are straight chain or branched divalent alkylene radicals. Examples which may be mentioned are the butylene, isobutylene, sec-butylene, tert-butylene, propylene, isopropylene, ethylene and the methylene radical.

An 1–4C-alkylcarbonylamino radical is, for example, the propionylamino [C$_3$H$_7$C(O)NH—] and the acetylamino radical [CH$_3$C(O)NH—].

4–8C-cycloalkylene stands for cyclobutylene, cyclopentylene, cyclohexylene, cycloheptylene or cyclooctylene. Preferred examples are 1,4-cyclohexylene and 1,3-cyclohexylene.

Azacycloalkylene stands for a divalent 5–7C-cycloalkylene radical, in which one or two of the ring carbon atoms are substituted by a nitrogen atom. Examples which may be mentioned are the 4,1-piperidinylene, the 1,4-piperidinylene, the 1,4-homopiperazinylene, the 1,4-piperazinylene and the 3,1-pyrrolidinylene radical.

Mono- or Di-1–4C-alkylamino radicals contain in addition to the nitrogen atom, one or two of the above-mentioned 1–4C-alkyl radicals. Examples which may be mentioned are the di-1–4C-alkylamino radicals, especially the dimethylamino, the diethylamino and the diisopropylamino radical.

Mono- or Di-1–4C-alkylaminocarbonyloxy radicals contain in addition to the carbonyl group one of the above-mentioned mono- or di-1–4C-alkylamino radicals. Examples which may be mentioned are the N-methyl- the N,N-dimethyl-, the N-ethyl-, the N-propyl-, the N,N-diethyl- and the N-isopropylaminocarbonyloxy radical.

1–4C-Alkylcarbonyloxy stands for a carbonyloxy group to which one of the above-mentioned 1–4C-alkyl radicals is bonded. An example is the acetoxy radical [CH$_3$C(O)—O—].

1–4C-Alkylsulfonylamino is a sulfonylamino (—SO$_2$—NH—) group to which one of the above-mentioned 1–4C-alkyl radicals is bonded. An example is the methanesulfonylamino radical (CH$_3$SO$_2$NH—).

1–4C-Alkylsulfonylmethyl is a sulfonylmethyl (—SO$_2$—CH$_2$—) group to which one of the above-mentioned 1–4C-alkyl radicals is bonded. An example is the methanesulfonylmethyl radical (CH$_3$SO$_2$CH$_2$—).

1–4C-Alkoxy-1–4C-alkyl stands for one of the above-mentioned 1–4C-alkyl radicals which is substituted by one of the above-mentioned 1–4C-alkoxy radicals. Examples which may be mentioned are the methoxymethyl, methoxyethyl and the butoxyethyl radical.

Ar$_2$ represents a 8-hydroxy-1H-quinolin-2-on-5-yl radical or a phenyl radical substituted by R9, R10 and R11. Examples which may be mentioned for the phenyl radical substituted by R9, R10 and R11 are phenyl, 4-amino-3-chloro-5-cyanophenyl, 4-hydroxy-3-hydroxymethylphenyl, 4-amino-3-cyanophenyl, 4-amino-3,5-dichlorophenyl, 4-amino-3-chloro-5-trifluoromethylphenyl, 4-aminophenyl, 3,4-dihydroxyphenyl, 3,5-dihydroxyphenyl, 3,5-bis-tolylcarbonyloxyphenyl, 4-hydroxy-3-ureido-phenyl, 3-formylamino-4-hydroxyphenyl, 4-hydroxyphenyl, 3-amino-5-hydroxyphenyl, 2-fluorophenyl, 3-amino-5-hydroxymethylphenyl 3,5-di-tert-butylcarbonyloxyphenyl, 3,5-di-isopropylcarbonyloxyphenyl, 2-chloro-4-hydroxyphenyl, 2-fluoro-4-hydroxyphenyl, 3-fluoro-4-hydroxyphenyl, 4-hydroxy-3-methoxyphenyl, 4-hydroxy-3-methylsulfonamidophenyl and 4-hydroxy-3-methylsulfonylmethylphenyl.

Preferred examples of Ar$_2$ are 4-amino-3-chloro-5-cyanophenyl, 4-hydroxy-3-hydroxymethylphenyl, 4-amino-3-cyanophenyl, 4-amino-3-chloro-5-trifluoromethylphenyl and 4-amino-3,5-dichlorophenyl.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are those in which $Ar_1$ represents a phenyl radical of formula (Ia) substituted by R1 and R2 or a dihydrobenzofuranyl radical of formula (Ib) substituted by R3, R4 and R5:

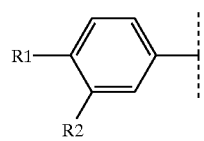
(Ia)

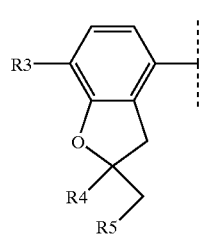
(Ib)

wherein
R1 is 1–4C-alkoxy or 1–4C-alkoxy which is completely or predominantly substituted by fluorine,
R2 is 1–4C-alkoxy, 3–5C-cycloalkoxy, 3–5C-cycloalkylmethoxy, or 1–4C-alkoxy which is completely or predominantly substituted by fluorine,
R3 is 1–4C-alkoxy, 3–5C-cycloalkoxy, 3–5C-cycloalkylmethoxy, or 1–4C-alkoxy which is completely or predominantly substituted by fluorine,
R4 is 1–4C-alkyl and
R5 is hydrogen or 1–4C-alkyl,
or wherein
R4 and R5 together and with inclusion of the two carbon atoms, to which they are bonded, form a spiro-linked cyclopentane, cyclohexane, tetrahydrofuran or tetrahydropyran ring, R6 and R7 represent independently from one another hydrogen or 1–4C-alkyl, or R6 and R7 together and with inclusion of the two carbon atoms, to which they are bonded, form a group selected from:

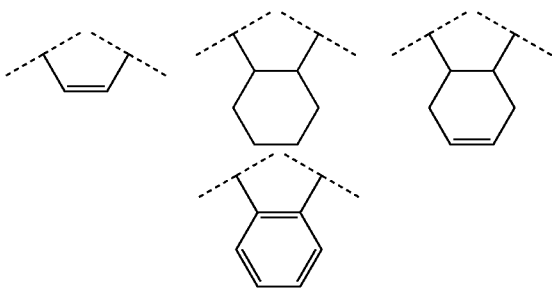

and A either represents $-C_mH_{2m}-Y-X-C_nH_{2n}-$, wherein either
X represents a bond,
Y represents a bond,
m is an integer from 1 to 4, and
n is an integer from 1 to 4,
or
X represents a bond, —O—, —S—, —C(O)—, —S(O)$_2$—, —C(O)—NH— or —C(S)—NH—,
Y represents 1,4-phenylene, 1,3-phenylene, 1,4-cyclohexylene, 1,3-cyclohexylene or 1,3-cyclopentylene,
m is an integer from 0 to 4, and
n is an integer from 1 to 4,
or
X represents a bond, —C(O)—, —S(O)$_2$—, —C(O)—NH— or —C(S)—NH—,
Y represents 4,1-piperidinylene,
m is 0, and
n is an integer from 1 to 4,
or
X represents a bond, —C(O)—, —S(O)$_2$—, —C(O)—NH— or —C(S)—NH—,
Y represents 1,4-piperazinylene,
m is an integer from 1 to 4, and
n is an integer from 1 to 4,
or
A represents $-Y-X-C_mH_{2m}-Z-C_nH_{2n}-$, wherein
X represents a bond, —C(O)—, —S(O)$_2$—, —C(O)—NH— or —C(S)—NH—,
Y represents 4,1-piperidinylene,
Z represents a bond, —O—, —S—, —S(O)$_2$— or —C(O)—NH—,
m is an integer from 1 to 4, and
n is an integer from 1 to 4,
or
X represents a bond, —O—, —S—, —C(O)—, —S(O)$_2$—, —C(O)—NH— or —C(S)—NH—,
Y represents 1,4-phenylene, 1,3-phenylene, 1,4-cyclohexylene, 1,3-cyclohexylene or 1,3-cyclopentylene,
Z represents a bond, —O—, —S—, —S(O)$_2$— or —C(O)—NH—,
m is an integer from 1 to 4, and
n is an integer from 1 to 4, R8 is hydrogen, methyl or ethyl,
Ar2 represents a 8-hydroxy-1H-quinolin-2-on-5-yl radical or a phenyl radical substituted by R9, R10 and R11, wherein
R9 is hydrogen, halogen, hydroxyl, amino, ureido [—NH—C(O)—NH$_2$], formylamino [—NH—C(O)H], 1–4C-alkylcarbonylamino, di-1–4C-alkylaminocarbonyloxy, tolylcarbonyloxy [—O—C(O)—C$_6$H$_4$—CH$_3$], hydroxymethyl, 1–4C-alkylcarbonyloxy, 1–4C-alkyl, 1–4C-alkoxy, 1–4C-alkylsulfonylamino, 1–4C-alkylsulfonylmethyl or 1–4C-alkoxy-1–4C-alkyl,
R10 is hydrogen, halogen, hydroxyl, cyano, trifluoromethyl, tolylcarbonyloxy [—O—C(O)—C$_6$H$_4$—CH$_3$], hydroxymethyl or 1–4C-alkylcarbonyloxy,
R11 is hydrogen or halogen,
and the salts of these compounds.

Compounds of the formula I which are particularly to be emphasized are those in which
Ar$_1$ represents a phenyl radical of formula (Ia) substituted by R1 and R2 or a dihydrobenzofuranyl radical of formula (Ib) substituted by R3, R4 and R5:

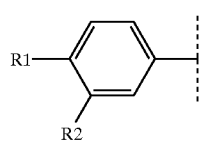

(Ia)

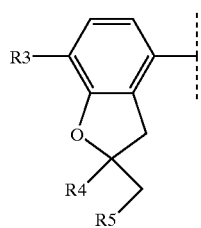

(Ib)

wherein
R1 is 1–2C-alkoxy or 1–2C-alkoxy which is completely or predominantly substituted by fluorine,
R2 is 1–2C-alkoxy, 3–5C-cycloalkoxy, 3–5C-cycloalkylmethoxy, or 1–2C-alkoxy which is completely or predominantly substituted by fluorine,
R3 is 1–2C-alkoxy or 1–2C-alkoxy which is completely or predominantly substituted by fluorine,
R4 is methyl and
R5 is hydrogen,
or wherein
R4 and R5 together and with inclusion of the two carbon atoms, to which they are bonded, form a spiro-linked cyclopentane or cyclohexane ring,
R6 and R7 together and with inclusion of the two carbon atoms, to which they are bonded, form a group selected from:

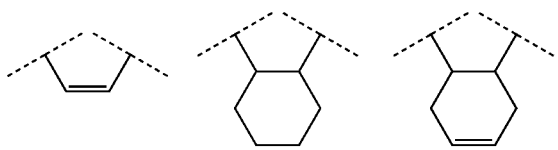

and A either represents —C$_m$H$_{2m}$—Y—X—C$_n$H$_{2n}$—, wherein either
X represents a bond,
Y represents a bond,
m is an integer from 1 to 4, and
n is an integer from 1 to 4,
or
X represents a bond, —O— or —C(O)—NH—,
Y represents 1,4-phenylene or 1,4-cyclohexylene,
m is an integer from 0 to 4, and
n is an integer from 1 to 4,
or
X represents a bond, —C(O)—, —S(O)$_2$— or —C(S)—NH—,
Y represents 4,1-piperidinylene,
m is 0, and
n is an integer from 1 to 4,
or
A represents —Y—X—C$_m$H$_{2m}$—Z—C$_n$H$_{2n}$—, wherein either
X represents a bond or —C(O)—,
Y represents 4,1-piperidinylene,
Z represents a bond, —S— or —S(O)$_2$—,
m is an integer from 1 to 4, and
n is an integer from 1 to 4,
or
X represents a bond, —O— or —C(O)—NH—,
Y represents 1,4-phenylene or 1,4-cyclohexylene,
Z represents a bond,
m is an integer from 1 to 4, and
n is an integer from 1 to 4,
R8 is hydrogen,
Ar$_2$ represents a 8-hydroxy-1H-quinolin-2-on-5-yl radical or a phenyl radical substituted by R9, R10 and R11, wherein
R9 is hydrogen, hydroxyl or amino,
R10 is hydrogen, halogen, cyano, trifluoromethyl or hydroxymethyl,
R11 is hydrogen or halogen,
and the salts of these compounds.

Preferred compounds of formula I are those in which
Ar$_1$ represents a phenyl radical of formula (Ia) substituted by R1 and R2 or a dihydrobenzofuranyl radical of formula (Ib) substituted by R3, R4 and R5:

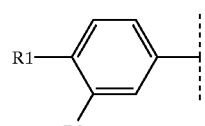

(Ia)

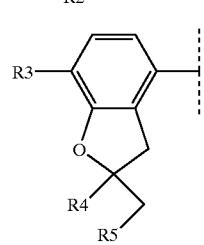

(Ib)

wherein
R1 is methoxy or ethoxy,
R2 is methoxy or ethoxy,
R3 is methoxy,
R4 and R5 together and with inclusion of the two carbon atoms, to which they are bonded, form a spiro-linked cyclopentane ring, R6 and R7 together and with inclusion of the two carbon atoms, to which they are bonded, form a group selected from:

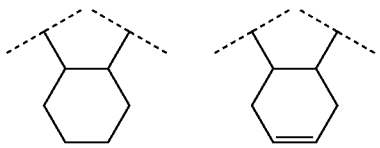

and A either represents —$C_mH_{2m}$—Y—X—$C_nH_{2n}$—, wherein either

X represents a bond,

Y represents a bond, m is an integer from 1 to 4, and n is an integer from 1 to 4, or X represents a bond, —O— or —C(O)—NH—, Y represents 1,4-phenylene, m is an integer from 0 to 1, and n is an integer from 1 to 4, or X represents a bond, —C(O)—, —S(O)$_2$— or —C(S)—NH—, Y represents 4,1-piperidinylene, m is 0, and n is an integer from 1 to 4, or A represents —Y—X—$C_mH_{2m}$—Z—$C_nH_2$—, wherein X represents a bond or —C(O)—, Y represents 4,1-piperidinylene, Z represents a bond, —S— or —S(O)$_2$—, m is 2 or 3, and n is 2 or 3, R8 is hydrogen, Ar$_2$ is phenyl, 4-amino-3-chloro-5-cyanophenyl, 4-amino-3-chloro-5-trifluoromethylphenyl, 4-hydroxy-3-hydroxymethylphenyl, 4-amino-3-cyanophenyl or 4-amino-3,5-dichlorophenyl, and the salts of these compounds.

One embodiment (embodiment A) of the compounds of formula I are those, in which

Ar$_1$ represents a phenyl radical of formula (Ia) substituted by R1 and R2 or a dihydrobenzofuranyl radical of formula (Ib) substituted by R3, R4 and R5:

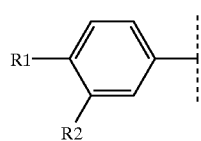

(Ia)

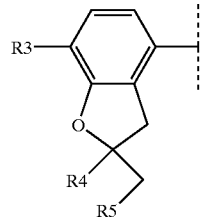

(Ib)

wherein

R1 is hydroxyl, halogen, 1–4C-alkoxy or 1–4C-alkoxy which is completely or predominantly substituted by fluorine, R2 is hydroxyl, halogen, 1–8C-alkoxy, 3–7C-cycloalkoxy, 3–7C-cycloalkylmethoxy, or 1–4C-alkoxy which is completely or predominantly substituted by fluorine, R3 is 1–4C-alkoxy, 3–5C-cycloalkoxy, 3–5C-cycloalkylmethoxy, or 1–4C-alkoxy which is completely or predominantly substituted by fluorine, R4 is 1–4C-alkyl and R5 is hydrogen or 1–4C-alkyl, or wherein R4 and R5 together and with inclusion of the two carbon atoms, to which they are bonded, form a spiro-linked 5-, 6- or 7-membered hydrocarbon ring, optionally interrupted by an oxygen or sulphur atom, R6 and R7 represent independently from one another hydrogen or 1–4C-alkyl, or R6 and R7 together and with inclusion of the two carbon atoms, to which they are bonded, form a group selected from:

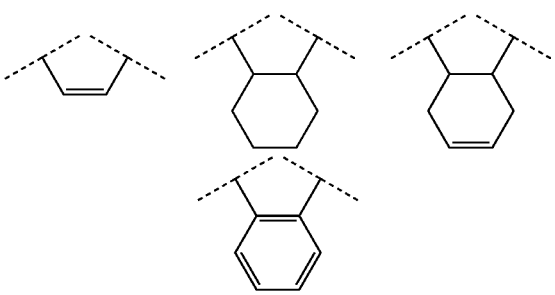

A represents —$(CH_2)_m$—Y—X—$(CH_2)_n$—, wherein

X represents a bond, —O— (oxygen), —S— (sulfur), —NH—, —C(O)—, —C(O)—NH— or —NH—C(O)—NH—, Y represents a bond, phenylene, 4–8C-cycloalkylene or azacycloalkylene, m is an integer from 0 to 4, n is an integer from 1 to 4, R8 is hydrogen or 1–4C-alkyl, Ar$_2$ represents a 8-hydroxy-1H-quinolin-2-on-5-yl radical or a phenyl radical substituted by R9, R10 and R11, wherein R9 is hydrogen, halogen, hydroxyl, amino, ureido [—NH—C(O)—NH$_2$], formylamino [—NH—C(O)H], 1–4C-alkylcarbonylamino, di-1–4C-alkylaminocarbonyloxy, tolylcarbonyloxy [—O—C(O)—$C_6H_4$—CH$_3$], hydroxymethyl, 1–4C-alkylcarbonyloxy, 1–4C-alkyl, 1–4C-alkoxy, 1–4C-alkylsulfonylamino, 1–4C-alkylsulfonylmethyl or 1–4C-alkoxy-1–4C-alkyl, R10 is hydrogen, halogen, hydroxyl, cyano, trifluoromethyl, tolylcarbonyloxy [—O—C(O)—$C_6H_4$—CH$_3$], hydroxymethyl or 1–4C-alkylcarbonyloxy, R11 is hydrogen or halogen,
and the salts of these compounds.

Compounds of the formula I of embodiment A to be emphasized are those in which

Ar₁ represents a phenyl radical of formula (Ia) substituted by R1 and R2 or a dihydrobenzofuranyl radical of formula (Ib) substituted by R3, R4 and R5:

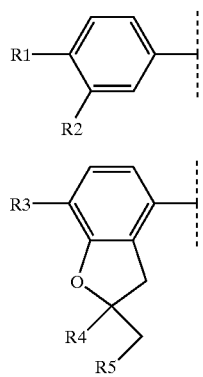

wherein
R1 is 1–4C-alkoxy or 1–4C-alkoxy which is completely or predominantly substituted by fluorine,
R2 is 1–4C-alkoxy, 3–5C-cycloalkoxy, 3–5C-cycloalkylmethoxy, or 1–4C-alkoxy which is completely or predominantly substituted by fluorine,
R3 is 1–4C-alkoxy, 3–5C-cycloalkoxy, 3–5C-cycloalkylmethoxy, or 1–4C-alkoxy which is completely or predominantly substituted by fluorine,
R4 is 1–4C-alkyl and
R5 is hydrogen or 1–4C-alkyl,
or wherein
R4 and R5 together and with inclusion of the two carbon atoms, to which they are bonded, form a spiro-linked cyclopentane, cyclohexane, tetrahydrofuran or tetrahydropyran ring,
R6 and R7 represent independently from one another hydrogen or 1–4C-alkyl, or R6 and R7 together and with inclusion of the two carbon atoms, to which they are bonded, form a group selected from:

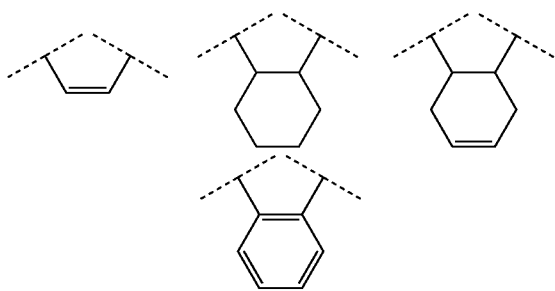

A represents —(CH₂)$_m$—Y—X—(CH₂)$_n$—, wherein
X represents a bond, —O— (oxygen), —NH—, —C(O)— or —C(O)—NH—,
Y represents a bond, phenylene, cyclopentylene, cyclohexylene, piperidinylene or piperazinylene,
m is an integer from 0 to 4,
n is an integer from 1 to 4,
R8 is hydrogen, methyl or ethyl,
Ar₂ represents a 8-hydroxy-1H-quinolin-2-on-5-yl radical or a phenyl radical substituted by R9, R10 and R11, wherein R9 is hydrogen, halogen, hydroxyl, amino, ureido [—NH—C(O)—NH₂], formylamino [—NH—C(O)H], 1–4C-alkylcarbonylamino, di-1–4C-alkylaminocarbonyloxy, tolylcarbonyloxy [—OC(O)—C₆H₄—CH₃], hydroxymethyl, 1–4C-alkylcarbonyloxy, 1–4C-alkyl, 1–4C-alkoxy, 1–4C-alkylsulfonylamino, 1–4C-alkylsulfonylmethyl or 1–4C-alkoxy-1–4C-alkyl,
R10 is hydrogen, halogen, hydroxyl, cyano, trifluoromethyl, tolylcarbonyloxy [—O—C(O)—C₆H₄—CH₃], hydroxymethyl or 1–4C-alkylcarbonyloxy,
R11 is hydrogen or halogen,
and the salts of these compounds.

Compounds of the formula I of embodiment A which are particularly to be emphasized are those in which Ar₁ represents a phenyl radical of formula (Ia) substituted by R1 and R2 or a dihydrobenzofuranyl radical of formula (Ib) substituted by R3, R4 and R5:

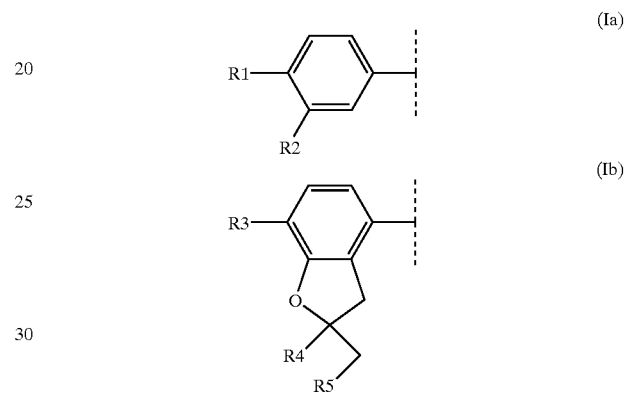

wherein
R1 is 1–2C-alkoxy or 1–2C-alkoxy which is completely or predominantly substituted by fluorine,
R2 is 1–2C-alkoxy, 3–5C-cycloalkoxy, 3–5C-cycloalkylmethoxy, or 1–2C-alkoxy which is completely or predominantly substituted by fluorine,
R3 is 1–2C-alkoxy or 1–2C-alkoxy which is completely or predominantly substituted by fluorine,
R4 is methyl and
R5 is hydrogen,
or wherein
R4 and R5 together and with inclusion of the two carbon atoms, to which they are bonded, form a spiro-linked cyclopentane or cyclohexane ring,
R6 and R7 together and with inclusion of the two carbon atoms, to which they are bonded, form a group selected from:

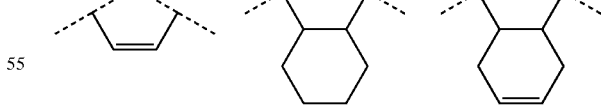

A represents —(CH₂)$_m$—Y—X—(CH₂)$_n$—, wherein
X represents a bond or —C(O)—,
Y represents a bond, 1,4-phenylene, 1,4-cyclohexylene or 4,1-piperidinylene,
m is an integer from 0 to 4,
n is an integer from 1 to 4,
R8 is hydrogen,
Ar₂ represents a 8-hydroxy-1H-quinolin-2-on-5-yl radical or a phenyl radical substituted by R9, R10 and R11, wherein R9 is hydrogen, hydroxyl or amino,
R10 is hydrogen, halogen, cyano, trifluoromethyl or hydroxymethyl,
R11 is hydrogen or halogen,
and the salts of these compounds.

Preferred compounds of formula I of embodiment A are those in which
$Ar_1$ represents a phenyl radical of formula (Ia) substituted by R1 and R2 or a dihydrobenzofuranyl radical of formula (Ib) substituted by R3, R4 and R5:

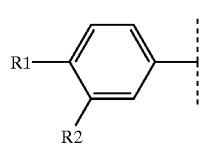

(Ia)

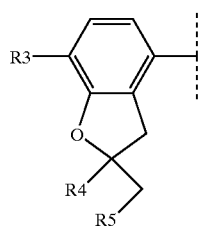

(Ib)

wherein
R1 is methoxy, ethoxy or difluoromethoxy,
R2 is methoxy or ethoxy,
R3 is methoxy,
R4 and R5 together and with inclusion of the two carbon atoms, to which they are bonded, form a spiro-linked cyclopentane ring,
R6 and R7 together and with inclusion of the two carbon atoms, to which they are bonded, form a group selected from:

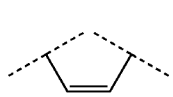 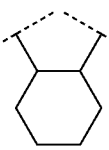 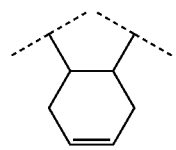

A represents —$(CH_2)_m$—Y—X—$(CH_2)_n$—, wherein
X represents a bond,
Y represents a bond or 1,4-phenylene,
m is an integer from 0 to 4,
n is an integer from 1 to 4,
R8 is hydrogen,
$Ar_2$ is phenyl, 4-amino-3-chloro-5-cyanophenyl, 4-amino-3-chloro-5-trifluoromethylphenyl, 4-hydroxy-3-hydroxymethylphenyl, 4-amino-3-cyanophenyl or 4-amino-3,5-dichlorphenyl,
and the salts of these compounds.

For the purpose of this invention the following numbering is used in the phthalazinone respectively pyridazinone part of the compounds of formula I:

Numbering Pyridazinone Compounds

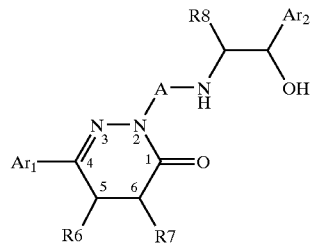

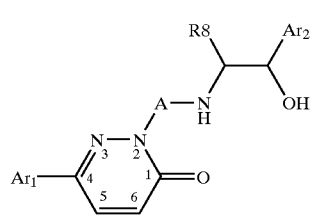

Numbering Phthalazinone Compounds

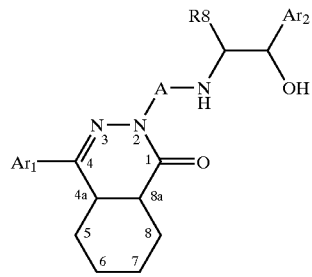

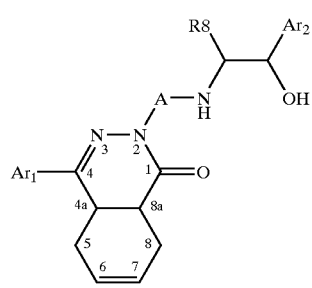

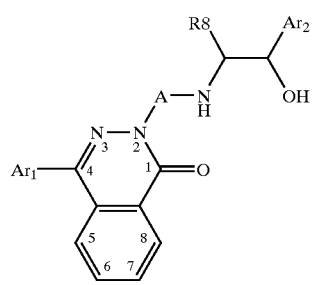

The compounds of formula I are chiral compounds with—depending of the meaning of Ar₁—a chiral center in the dihydrobenzofuranyl radical, if the substituents —R4 and —CH₂R5 are not identical. However, preferred are those compounds, in which the substituents —R4 and —CH₂R5 are identical or together and with inclusion of the carbon atoms to which they are bonded form a spiro-connected 5-, 6- or 7-membered hydrocarbon ring.

Further possible chiral centers in the compounds of formula I are marked in the following formula I* with an asterix (*):

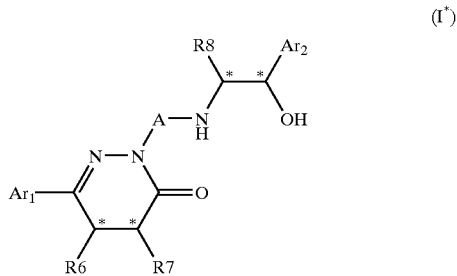

The invention includes all conceivable pure diastereomers and pure enantiomers, as well as all mixtures thereof independent from the ratio, including the racemates.

In those cases, wherein R6 and R7 together and with inclusion of the two carbon atoms, to which they are bonded, form a group selected from:

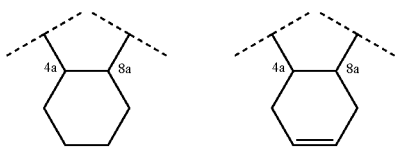

those compounds are preferred, in which the hydrogen atoms in the positions 4a and 8a are cis-configurated. Especially preferred in this connection are those compounds, in which the absolute configuration (according to the rules of Cahn, Ingold and Prelog) is S in the position 4a and R in the position 8a.

(4a,8a)-cis-Racemates can be split up into the corresponding enantiomers by methods known by a person skilled in the art. Preferably the racemic mixtures are separated into two diastereomers during the preparation with the help of an optical active separation agent on the stage of the cyclohexane-carboxylic acids or the 1,2,3,6-tetrahydrobenzoic acids. As separation agents may be mentioned, for example, optical active amines such as the (+)- and (−)-forms of 1-phenylethylamine [(R)-(+)-1-phenylethylamine=D-α-methylbenzylamine or (S)-(−)-1-phenylethylamine=L-α-methylbenzylamine) and ephedrine, the optical active alkaloids quinine, cinchonine, cinchonidine and brucine.

The preparation of (4aS, 8aR) configurated 4-(3,4-dialkoxyphenyl)-4a,5,8,8a-tetrahydro-2H-phthalazin-1-ones or 4-(3,4-dialkoxyphenyl)-4a,5,6,7,8,8a-hexahydro-2H-phthalazin-1-ones is described, for example, in the international application WO98/31674.

The preparation of (4aS, 8aR) configurated 4-(2,3-dihydro-7-alkoxybenzofuran-2-spiro-1'-cyclopentan-4-yl)-4a,5,6,7,8,8a-hexahydro-2H-phthalazin-1-ones is described, for example, in the international application WO99/31090.

One group of preferred compounds of formula I are those in which the divalent radical A has a longitudinal extension of about 4 to about 6 carbon carbon bonds. Examples which may be mentioned in this connection are tetramethylene, pentamethylene, hexamethylene or phenylethylene.

Another group of preferred compounds of formula I are those in which Y represents a 1,4-phenylene or 4,1-piperidinylene radical.

The invention further relates to processes for the preparation of compounds of formula I and their salts.

Several alternative synthetic routes to compounds of formula I are described in the Reaction Schemes I to IX.

Reaction Scheme I describes the preparation of compounds of formula I starting from 2H-phthalazin-1-one or 2H-pyridazin-1-one compounds. These are reacted in a first reaction with appropriate α,ω-dihalogenalkanes (if A represents an alkylene chain) to give the corresponding 2-(ω-halogenalkyl)phthalazin-1-ones or 2-(ω-halogenalkyl) pyridazinones. In a second reaction these compounds are then converted to compounds of formula I through reaction with an 2-amino-1-(phenyl)ethanol derivative. Compounds of formula I in which A contains additional to the alkylene chain further groups, for example a 1,4-phenylene radical, can be prepared in an analogous manner.

Reaction Scheme I:

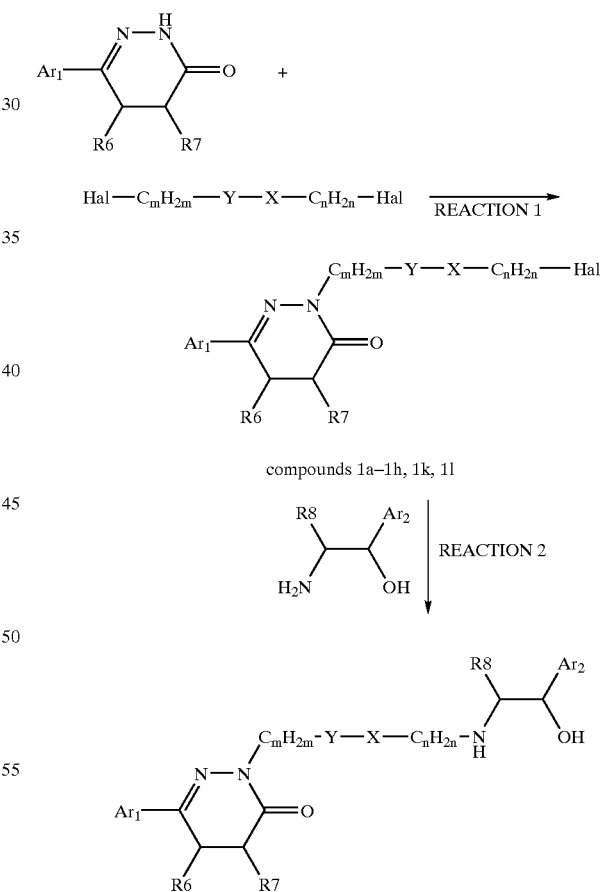

[particularly suitable for compounds of formula I, in which
A represents —$C_mH_{2m}$—Y—X—$C_nH_{2n}$— wherein
X represents a bond,
Y represents a bond, phenylene or 4–8C-cycloalkylene,
m is an integer from 0 to 4,
n is an integer from 1 to 4]

Reaction Scheme II:

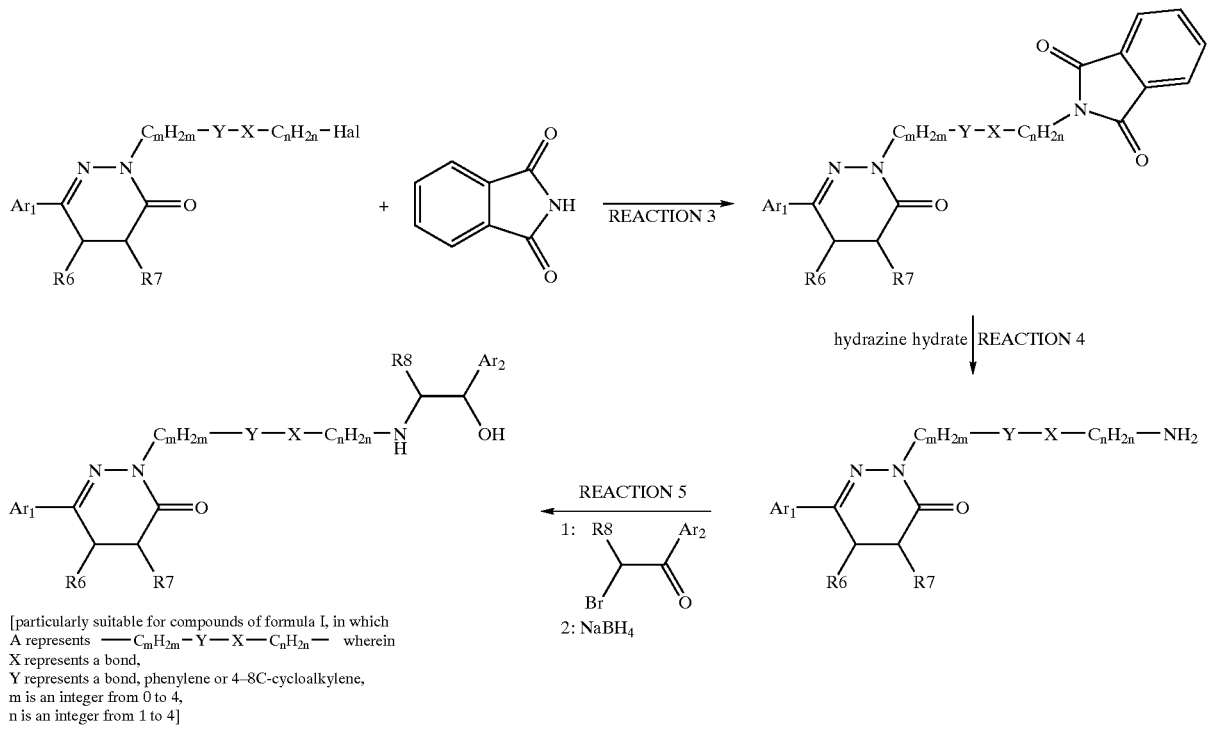

[particularly suitable for compounds of formula I, in which
A represents —$C_mH_{2m}$—Y—X—$C_nH_{2n}$— wherein
X represents a bond,
Y represents a bond, phenylene or 4–8C-cycloalkylene,
m is an integer from 0 to 4,
n is an integer from 1 to 4]

Reaction Scheme II starts with the 2-(ω-halogenalkyl) phthalazin-1-ones or 2-(ω-halogenalkyl)pyridazinones already described in Reaction Scheme I. In a first reaction the halogen atom is replaced by an amino group via a Gabriel synthesis (for example as described in Angew. Chem. 80, 986–996). The 1-(phenyl)ethanol part of the compounds of formula I is introduced with the help of a 2-bromoacetophenone derivative followed by a reduction step.

Reaction Scheme III also starts with the 2-(ω-halogenalkyl)phthalazin-1-ones or 2-(ω-halogenalkyl) pyridazinones already described in Reaction Scheme I. In this alternative the amino function is introduced through reaction with benzylamine. The 1-(phenyl)ethanol part of the compounds of formula I is again introduced with the help of a 2-bromoacetophenone derivative followed by a reduction step. Finally the benzyl group is removed, for example, by catalytic hydrogenation.

Reaction Scheme III:

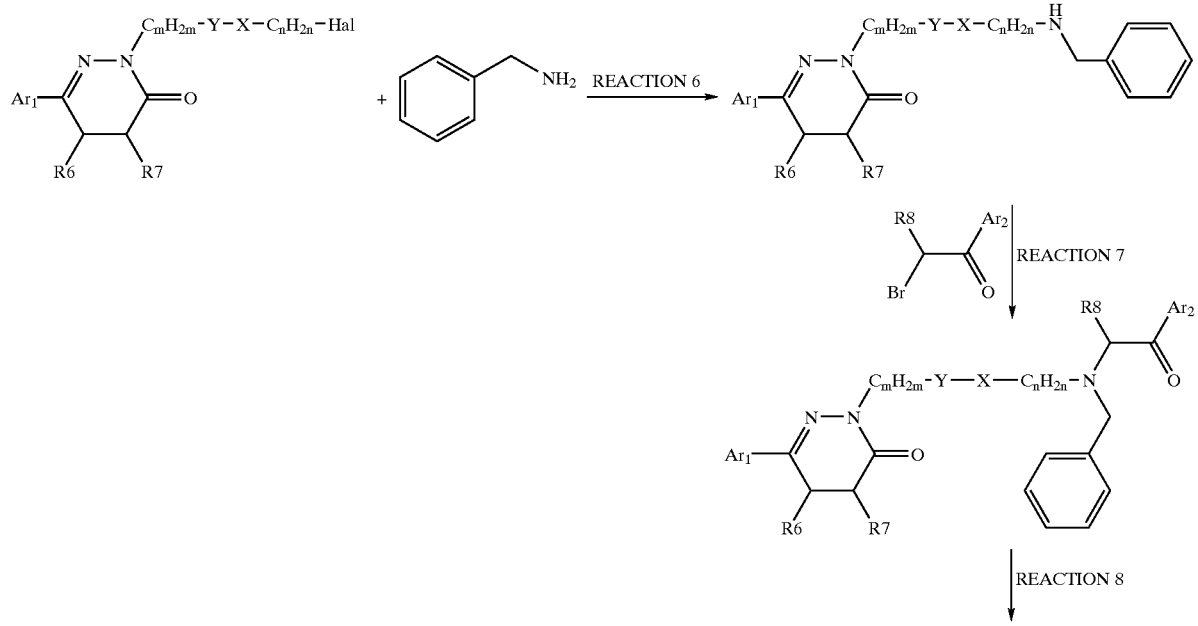

-continued

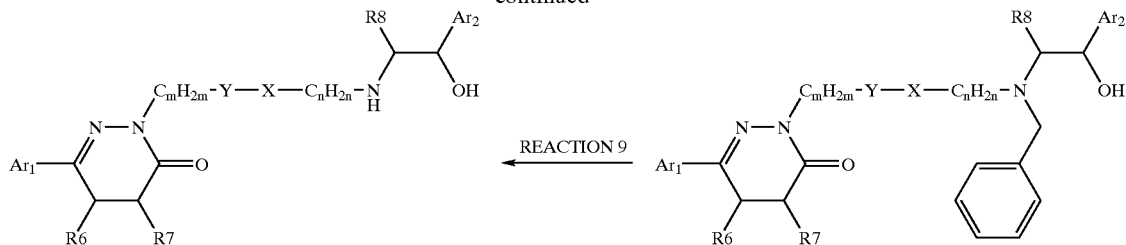

REACTION 9

[particularly suitable for compounds of formula I, in which
A represents —$C_mH_{2m}$—Y—X—$C_nH_{2n}$— wherein
X represents a bond,
Y represents a bond, phenylene or 4–8C-cycloalkylene,
m is an integer from 0 to 4,
n is an integer from 1 to 4]

Reaction scheme IV:
Exemplarily shown is X = —O— and Y = phenylene:

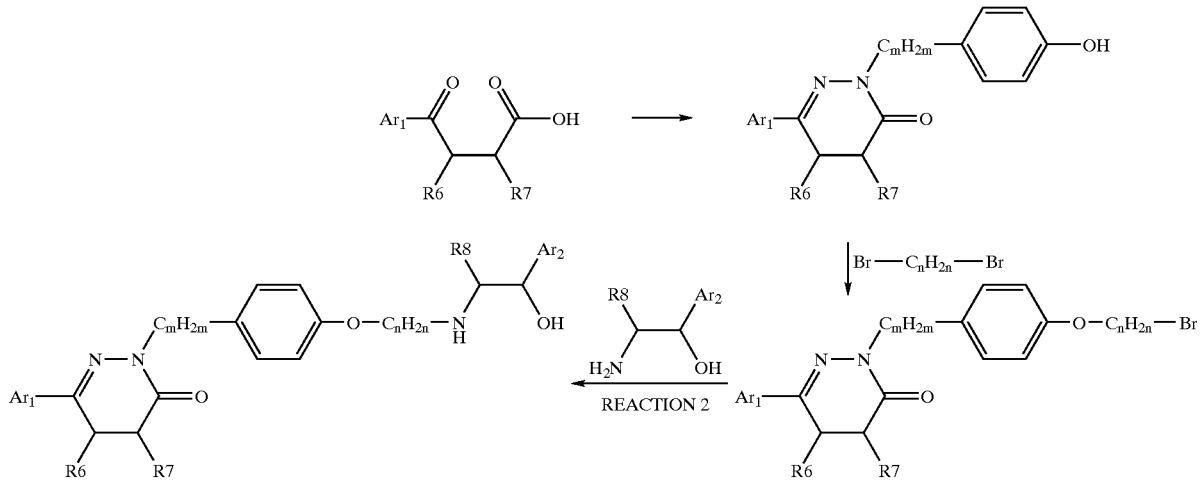

REACTION 2

[particularly suitable for compounds of formula I, in which
A represents —$C_mH_{2m}$—Y—X—$C_nH_{2n}$— wherein
X represents —O— (oxygen) or —S— (sulfur)
Y represents phenylene or 4–8C-cycloalkylene,
m is an integer from 0 to 4,
n is an integer from 1 to 4];

Reaction scheme V:
Exemplarily shown is X = —C(O)— and Y = 4,1-piperidinylene:

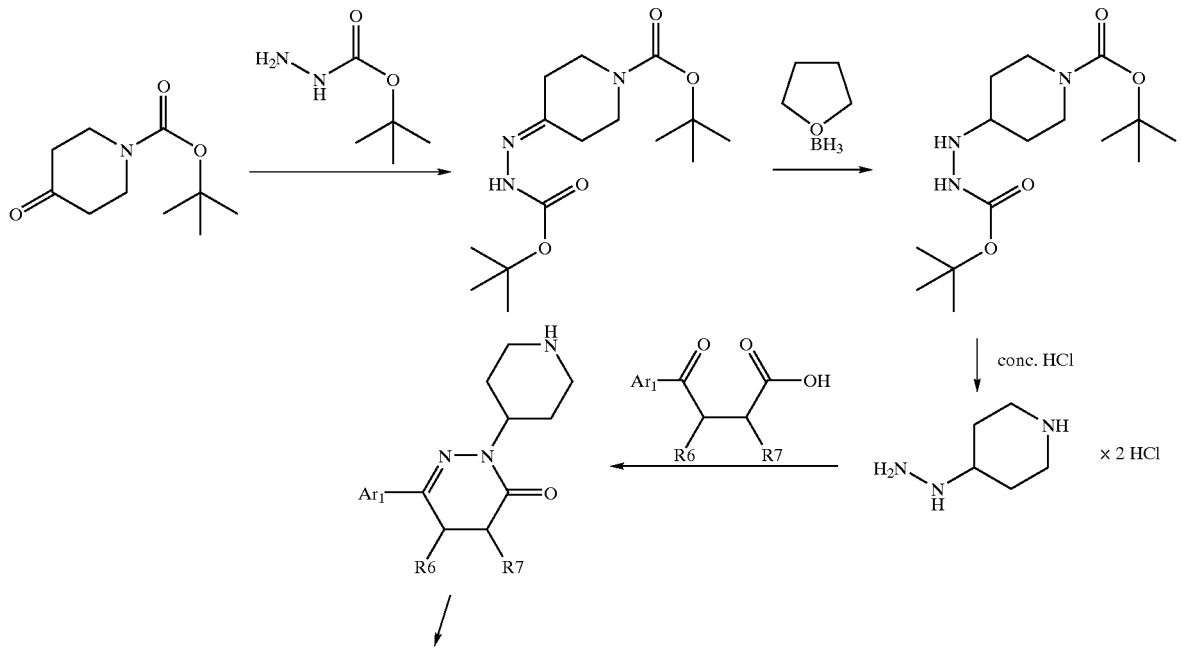

conc. HCl

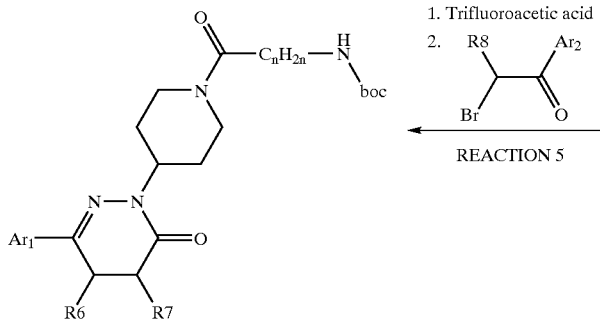

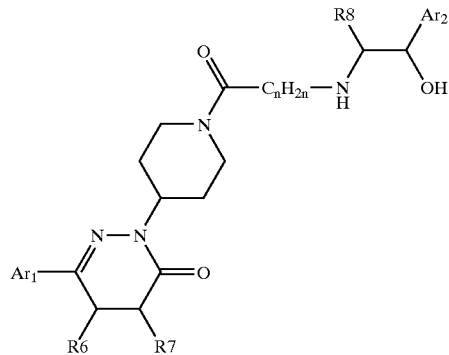

REACTION 5

1. Trifluoroacetic acid
2. 
[R8, Ar2, Br, O structure]

[particularly suitable for compounds of formula I, in which
A represents —$C_mH_{2m}$—Y—X—$C_nH_{2n}$—, wherein
X represents —C(O)— or —$S(O)_2$—,
Y represents azacycloalkylene,
m is 0,
n is an integer from 1 to 4];

Reaction scheme VI:
Exemplarily shown is Y = 4,1-piperidinylene:

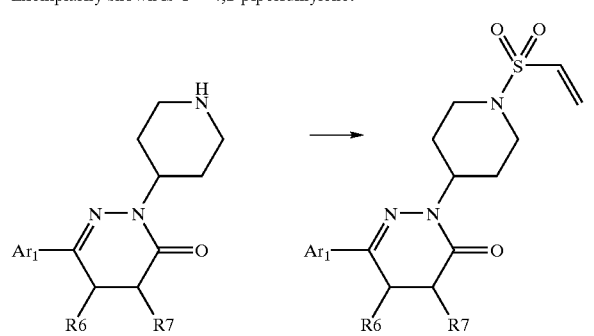

REACTION 10

Reaction scheme VII:
Exemplarily shown is Y = 4,1-piperidinylene:

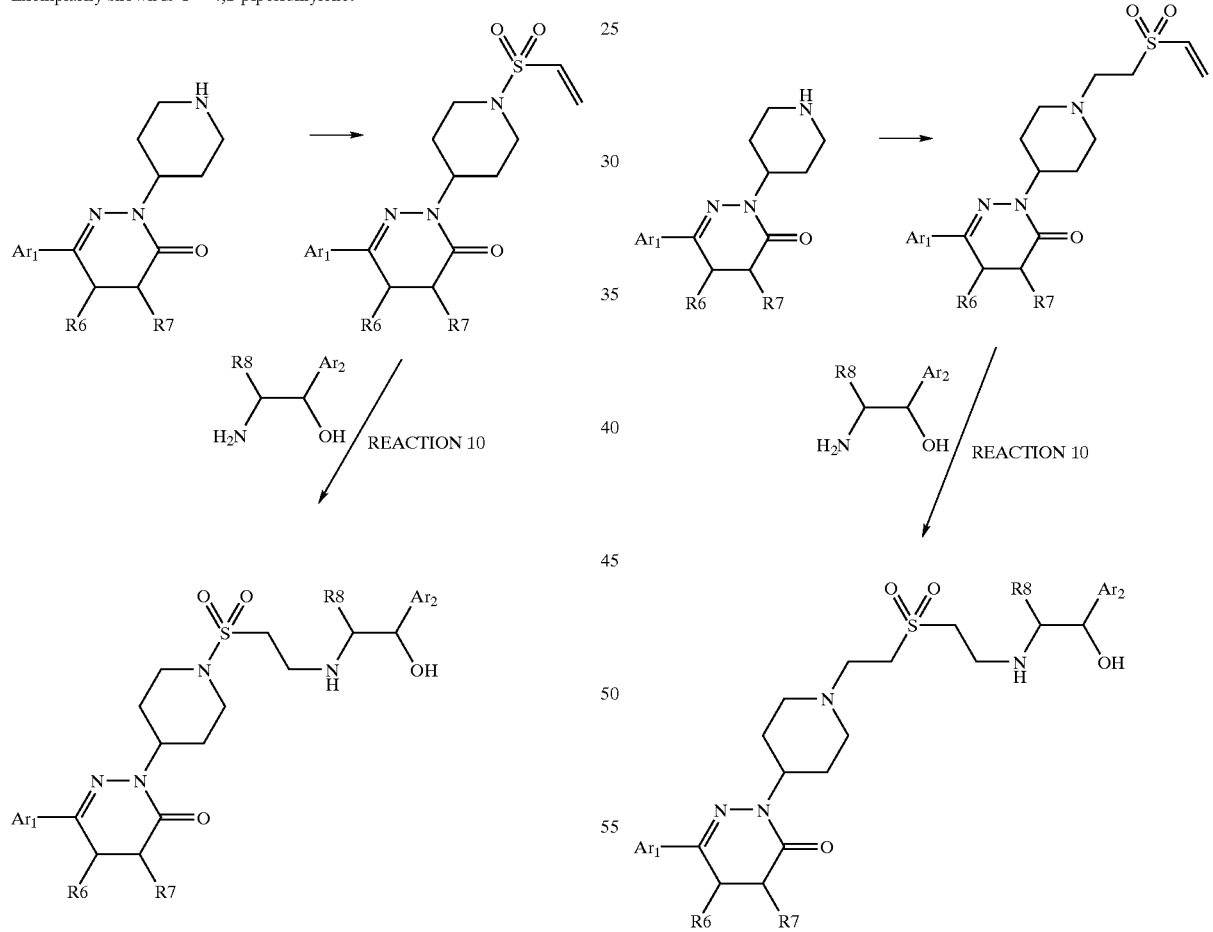

REACTION 10

[particularly suitable for compounds of formula I, in which
A represents —$C_mH_{2m}$—Y—X—$C_nH_{2n}$—, wherein
X represents —$S(O)_2$—,
Y represents azacycloalkylene,
m is 0,
n is 2]

[particularly suitable for compounds of formula I, in which
A represents —Y—X—$C_mH_{2m}$—Z—$C_nH_{2n}$—, wherein
X represents a bond,
Y represents azacycloalkylene,
Z represents —$S(O)_2$—,
m is an integer from 1 to 4,
n is 2];

Reaction scheme VIII:
Exemplarily shown is Y = 4,1-piperidinylene and Z = —S— or —S(O)$_2$—:
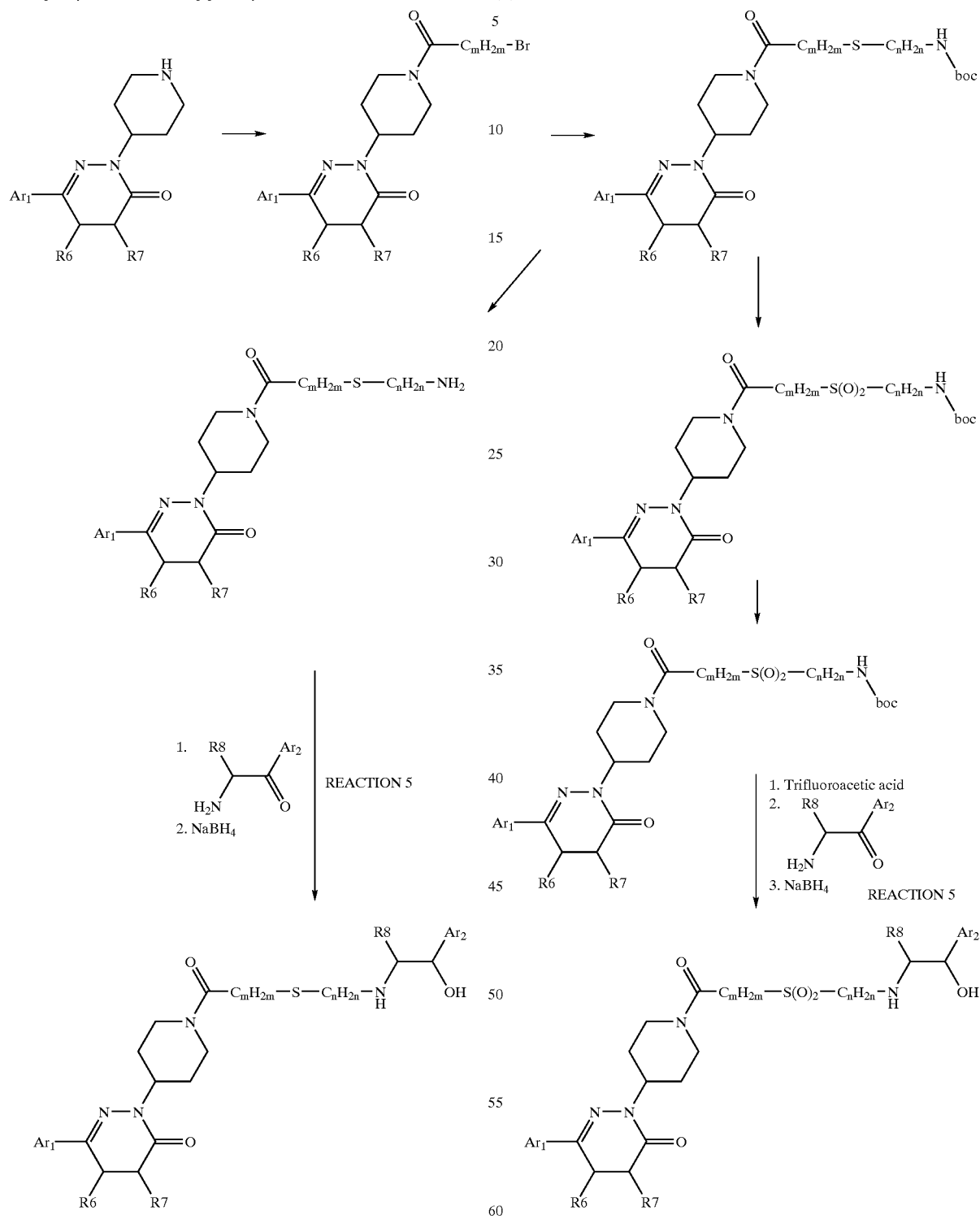
[particularly suitable for compounds of formula I, in which
A represents —Y—X—C$_m$H$_{2m}$—Z—C$_n$H$_{2n}$— wherein,
X represents —C(O)—,
Y represents azacycloalkylene,
Z represents —O—, —S— or —S(O)$_2$—,
m is an integer from 1 to 4,
n is an integer from 1 to 4];

Reaction scheme IX:
Exemplarily shown is X = —NH—C(S)—NH—,
and Y = phenylene:

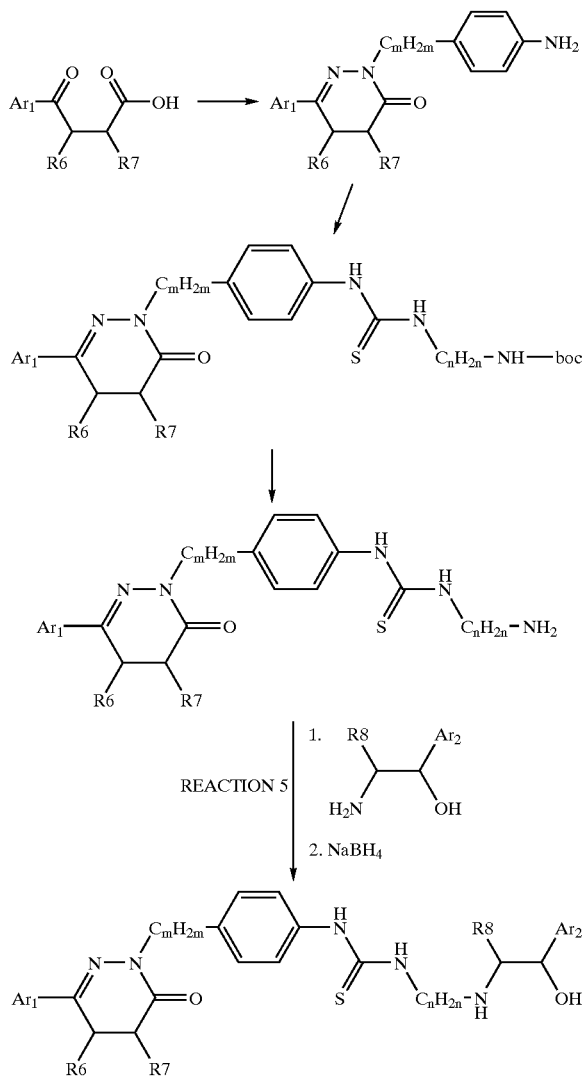

[particularly suitable for compounds of formula I, in which
A represents —$C_mH_{2m}$—Y—X—$C_nH_{2n}$—, wherein
X represents —NH—C(O)—NH— or
—NH—C(S)—NH—,
Y represents phenylene or 4–8C-cycloalkylene,
m is an integer from 0 to 4,
n is an integer from 1 to 4];

Further compounds of formula I, whose preparation is not explicitly described in the above reaction schemes can be prepared analogously to the methods described in the following examples or according to customary preparation methods known to the person skilled in the art.

All the starting compounds are known or can be prepared according to customary preparation methods known to the person skilled in the art.

The preparation of appropriate starting compounds with a phthalazinone structure is described for example in WO98/31674, WO99/31090 or EP0934933. The preparation of appropriate starting compounds with a pyridazinone structure is described for example in EP0163965.

Suitably, the conversions are carried out analogous to methods which are familiar per se to the person skilled in the art, for example, in the manner which is described in the following examples.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. W. Greene, Protective groups in organic Synthesis, John Wiley & Sons, 1991.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn, can be converted into salts. In this manner, pharmacologically non-tolerable salts can be converted into pharmacologically tolerable salts.

The following examples illustrate the invention in greater detail, without restricting it. The compounds, which are mentioned in the examples as well as their salts are preferred compounds of the invention.

EXAMPLES

Final Products 1. (cis)-2-(4-[{2-(4-amino-3,5-dichlorophenyl)-2-hydroxyethyl}-amino]-1-butyl)-4-(3,4-dimethoxyphenyl)-4a,5,6,7,8,8a-hexahydro-2H-phthalazin-1-one fumarate Prepared from compound 1a and compound A according to REACTION 2. M. p. 85–88° C.

2. (cis)-2-(6-[{2-(4-amino-3,5-dichlorophenyl)-2-hydroxyethyl}-amino]-1-hexyl)-4-(3,4-dimethoxyphenyl)-4a,5,6,7,8,8a-hexahydro-2H-phthalazin-1-one hemifumarate Prepared from compound 1b and compound A according to REACTION 2. M. p. 110–112° C.

3. (cis)-2-(8-[{2-(4-amino-3,5-dichlorophenyl)-2-hydroxyethyl}-amino]-1-octyl)-4-(3,4-dimethoxyphenyl)-4a,5,6,7,8,8a-hexahydro-2H-phthalazin-1-one hemifumarate Prepared from compound 1c and compound A according to REACTION 2. M. p. 111–113° C.

4. (cis)-2-(6-[{2-(4-amino-3,5-dichlorophenyl)-2-hydroxyethyl}-amino]-1-hexyl)-4-(3,4-diethoxyphenyl)-4a,5,6,7,8,8a-hexahydro-2H-phthalazin-1-one hemifumarate Prepared from compound 1d and compound A according to REACTION 2. M. p. 109–111° C.

5. (cis)-2-{4-(2-[{2-(4-amino-3,5-dichlorophenyl)-2-hydroxyethyl}amino]-1-ethyl)phenyl)-4-(3,4-dimethoxyphenyl)-4a,5,8,8a-tetrahydro-2H-phthalazin-1-one hemifumarate Prepared from compound 1j and compound A according to REACTION 2. M. p. 121–125° C.

6. (cis)-2-(6-[{2-(4-amino-3,5-dichlorophenyl)-2-hydroxyethyl}-amino]-1-hexyl)-4-(3,4-dimethoxyphenyl)-4a,5,8,8a-tetrahydro-2H-phthalazin-1-one hemifumarate Prepared from compound 1e and compound A according to REACTION 2. M. p. 119–122° C.

7. (cis)-2-(6-[{2-(4-amino-3,5,dichlorophenyl)-2-hydroxyethyl}amino]-1-hexyl)-4-(3,4-dimethoxyphenyl)-2H-phthalazin-1-one hemifumarate Prepared from compound 1k and compound A according to REACTION 2. M. p. 107–110° C.

8. (cis)-2-(2-[{2-(4-amino-3,5-dichlorophenyl)-2-hydroxyethyl}amino]-1-ethyl)-4-(2,3-dihydro-7-methoxybenzofuran-2-spiro-1'-cyclopentan-4-yl)-4a,5,8,8a-tetrahydro-2H-phthalazin-1-one Prepared from compound 1i and compound A according to REACTION 2. M. p. 176–177° C.

9. (cis)-2-(4-[{2-(4-amino-3,5-dichlorophenyl)-2-hydroxyethyl}amino]-1-butyl)-4-(2,3-dihydo-7-methoxybenzofuran-2-spiro-1'-cyclopentan-4-yl)-4a,5,8,8a-tetrahydro-2H-phthalazin-1-one hemifumarate Prepared from compound 1h and compound A according to REACTION 2. M. p. 120–123° C.

10. (cis)-2-(6-[{2-(4-amino-3,5,dichlorophenyl)-2-hydroxyethyl}amino]-1-hexyl)-6-(3-methoxy-4-difluoromethoxyphenyl)-2H-pyridazin-3-one hemifumarate Prepared from compound 11 and compound A according to REACTION 2. M. p. 80–85° C.

11. (cis)-2-(4-[{2-(4-amino-3-chloro-5-cyanophenyl)-2-hydroxyethyl}amino]-1-butyl)-4-(3, 4-dimethoxyphenyl)-4a,5,8,8a-tetrahydro-2H-phthalazin-1-one hemifumarate Prepared from compound 3b and compound D according to REACTION 5. M. p. 115–118° C.

12. (cis)-2-(5-[{2-(4-amino-3-chloro-5-cyanophenyl)-2-hydroxyethyl}amino]-1-pentyl)-4-(3,4-dimethoxyphenyl)-4a,5,8,8a-tetrahydro-2H-phthalazin-1-one hemifumarate Prepared from compound 3c and compound D according to REACTION 5. M. p. 121–123° C.

13. (cis)-2-(6-[{2-(4-amino-3-chloro-5-cyanophenyl)-2-hydroxyethyl}amino]-1-hexyl)-4-(3, 4-dimethoxyphenyl)-4a,5,8,8a-tetrahydro-2H-phthalazin-1-one hemifumarate Prepared from compound 3a and compound D according to REACTION 5. M. p. 168–170° C.

14. (cis)-4-(3,4-dimethoxyphenyl)-2-(6-[{2-(4-hydroxy-3-hydroxymethylphenyl)-2-hydroxyethyl}amino]-1-hexyl)-4a,5,6,7,8,8a-hexahydro-2H-phthalazin-1-one hemifumarate Prepared from compound 1b and compound C according to REACTION 2. M. p. 99–103° C.

15. (cis)-2-(8-[{2-(4-hydroxy-3-hydroxymethylphenyl)-2-hydroxyethyl}amino]-1-octyl)-4-(3,4-dimethoxyphenyl)-5,6,7,8,9,10-hexahydro-1-phthalazinone 3/4fumarate Prepared from compound 1c and compound C according to REACTION 2. M. p. 66–70° C.

16. (cis)-2-(6-[{2-(4-hydroxy-3-hydroxymethylphenyl)-2-hydroxyethyl}amino]-1-hexyl)-4-(3,4-dimethoxyphenyl)-4a,5,8,8a-tetrahydro-2H-phthalazin-1-one hemifumarate Prepared from compound 1e and compound C according to REACTION 2. M. p. 96–99° C.

17. (cis)-2-(6-[{2-(4-amino-3-chloro-5-trifluoromethylphenyl)-2-hydroxyethyl}amino]-1-hexyl)-4-(3,4-dimethoxyphenyl)-4a,5,6,7,8,8a-hexahydro-2H-phthalazin-1-one 3/4fumarate Prepared from compound 1b and compound B according to REACTION 2. M. p. 102–105° C.

18. (cis)-2-(6-[{2-(4-amino-3-cyanophenyl)-2-hydroxyethyl}amino]-1-hexyl)-4-(3,4-dimethoxyphenyl)-4a,5,6,7,8,8a-hexahydro-2H-phthalazin-1-one hemifumarate Prepared from compound 4 and compound E according to REACTIONS 7, 8 and 9. M. p. 101–103° C.

19. (cis)-4-(3,4-dimethoxyphenyl)-2-[6-{(2-phenyl-2-hydroxyethyl)amino}-1-hexyl]4a,5,6,7,8,8a-hexahydro-2H-phthalazin-1-one 3/4fumarate Prepared from compound 1b and 2-amino-1-phenylethanol according to REACTION 2. M. p. 110–115° C.

20. 2-Amino-3-chloro-5-[2-(4-{4-[(4aS,8aR)-4-(3,4-dimethoxy-phenyl)-1-oxo-4a,5,8,8a-tetrahydro-1H-phthalazin-2-yl]-piperidin-1-yl}-4-oxo-butylamino)-1-hydroxy-ethyl]-benzonitrile fumarate Prepared from starting compound 5a and starting compound D according to REACTION 5. M. p. 212–216° C.

21. (4aS,8aR)-2-(4-{4-[2-(4-Amino-3,5-dichlorophenyl)-2-hydroxy-ethylamino]-butoxyl}-phenyl)-4-(3,4-dimethoxy-phenyl)-4a,5,8,8a-tetrahydro-2H-phthalazin-1-one fumarate Prepared from compound 6a and compound A according to REACTION 2. M. p. 126–127° C.

22. (4aS,8aR)-2-(4-{4-[2-(4-Amino-3,5-dichloro-phenyl)-2-hydroxy-ethylamino]-butoxy}-benzyl)-4-(3,4-dimethoxy-phenyl)-4a,5,8,8a-tetrahydro-2H-phthalazin-1-one fumarate Prepared from compound 7a and compound A according to REACTION 2. M. p. 119–120° C.

23. (4aS,8aR)-2-(4-{2-[2-(4-Amino-3,5-dichloro-phenyl)-2-hydroxy-ethylamino]-ethoxy}-phenyl)-4-(3,4-dimethoxy-phenyl)-4a,5,8,8a-tetrahydro-2H-phthalazin-1-one oxalate Prepared from compound 8a and compound A according to REACTION 2. M. p. 136–138° C.

24. (4aS,8aR)-2-[1-(2-{2-[2-(4-Amino-3,5-dichloro-phenyl)-2-hydroxy-ethylamino]-ethanesulfonyl}-ethyl)-piperidin-4-yl]-4-(3,4-dimethoxy-phenyl)-4a,5,8,8a-tetrahydro-2H-phthalazin-1-one fumarate Prepared from compound 9a and compound A according to REACTION 10. M. p. 137–138° C.

25. 4-[(4aS,8aR)-4-(3,4-Dimethoxy-phenyl)-1-oxo-4a,5,8,8a-tetrahydro-1H-phthalazin-2-yl]-piperidine-1-carbothioic acid {4-[2-(4-amino-3,5-dichloro-phenyl)-2-hydroxy-ethylamino]-butyl}-amide Prepared from compound 10a and compound O according to REACTION 5. M. p. 139–144° C.

26. (4aS,8aR)-2-(1-{2-[2-(4-Amino-3,5-dichloro-phenyl)-2-hydroxy-ethylamino]-ethanoyl}-piperidin-4-yl)-4-(3,4-diethoxy-phenyl)-4a,5,8,8a-tetrahydro-2H-phthalazin-1-one fumarate Prepared from compound 11a and compound A according to REACTION 2. M. p. 172–173° C.

27. (4aS,8aR)-2-(1-{2-[2-(4-Amino-3,5-dichloro-phenyl)-2-hydroxy-ethylamino]-ethanesulfonyl}-piperidin-4yl)-4-(3,4-dimethoxy-phenyl)-4a,5,8,8a-tetrahydro-2H-phthalazin-1-one fumarate Prepared from compound 12a and compound A according to REACTION 2. M. p. 169–171° C.

28. (4aS,8aR)-2-(1-{(S)-2-[2-(3,4-Diamino-5-chloro-phenyl)-2-hydroxy-ethylamino]-propanoyl}-piperidin-4-yl)-4-(3,4-dimethoxy-phenyl)-4a,5,8,8a-tetrahydro-2H-phthalazin-1-one fumarate Prepared from compound 13a and compound O according to REACTION 5. M. p. 130–131° C.

29. (4aS,8aR)-4-(3,4-Dimethoxy-phenyl)-2-(1-{2-[2-hydroxy-2-(4-hydroxy-3-hydroxymethyl-phenyl)-ethylamino]-ethanesulfonyl}-piperidin-4-yl)-4a,5,8,8a-tetrahydro-2H-phthalazin-1-one Prepared from compound 12a and compound C according to REACTION 10. Crystallised as the free base from ethyl acetate. M. p. 97–99° C.

30. (4aS,8aR)-2-[1-(3-{2-[2-(4-Amino-3,5-dichloro-phenyl)-2-hydroxy-ethylamino]-ethylsulfanyl}-propanoyl)-piperidin-4-yl]-4-(3,4-dimethoxy-phenyl)-4a,5,8,8a-tetrahydro-2H-phthalazin-1-one hydrochloride Prepared from compound O and compound 14a according to REACTION 5. M. p. 118–120° C.

31. (4aS,8aR)-4-(3,4-Dimethoxy-phenyl)-2-(4-{4-[2-hydroxy-2-(4-hydroxy-3-hydroxymethyl-phenyl)-ethylamino]-butoxy}-phenyl)-4a,5,8,8a-tetrahydro-2H-phthalazin-1-one fumarate Prepared from compound 6a and compound C according to REACTION 2. M. p. 126–127° C.

32. 2-Amino-3-chloro-5-{2-[2-(3-{4-[(4aS,8aR)-4-(3,4-dimethoxy-phenyl)-1-oxo-4a,5,8,8a-tetrahydro-1H-phthalazin-2-yl]-piperidin-1-yl}-3-oxo-propane-1-sulfonyl)-ethylamino]-1-hydroxy-ethyl}-benzonitrile Prepared from compound 15a and compound D according to REACTION 5. Crystallised from diethyl ether as the free base. M. p. 102–103° C.

33. 2-Amino-3-chloro-5-[2-((S)-2-{4-[(4aS,8aR)-4-(3,4-dimethoxy-phenyl)-1-oxo-4a,5,8,8a-tetrahydro-1H-phthalazin-2-yl]-piperidin-1-yl}-1-methyl-2-oxo-ethylamino)-1-hydroxy-ethyl]-benzonitrile hydrochloride Prepared from compound 13a and compound D according to REACTION 5. Crystallised as the hydro-chloride. M. p. 160–161° C.

34. 2-Amino-3-chloro-5-[2-(6-{4-[(4aS,8aR)-4-(3,4-dimethoxy-phenyl)-1-oxo-4a,5,8,8a-tetrahydro-1H-phthalazin-2-yl]-piperidin-1-yl}-hexylamino)-1-hydroxy-ethyl]-benzonitrile fumarate Prepared from compound 16a and compound D according to REACTION 5. M. p. 142–143° C.

General Synthesis

Reaction 1

2-(ω-halogenalkyl)phthalazinones (compounds 1a–1h, 1k or 1l)

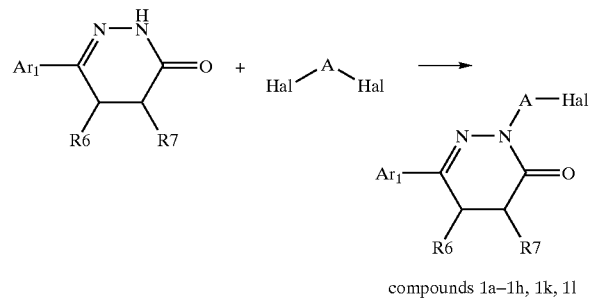

compounds 1a–1h, 1k, 1l 25 mmol of sodium hydride is added to a stirred solution of 20 mmol of a phthalazinone or a pyridazinone (compounds F–K) in 50 ml of dimethylformamide. After 5 min, 60 mmol of a α,ω-dihalogenalkane is added and the resulting mixture stirred for 60 min. After the addition of 200 ml of water, the mixture is extracted with diethyl ether. The ether solution is dried over magnesium sulfate and evaporated. The residue is purified by chromatography [ethyl acetate:petroleum ether (60–80° C.)/1:4].

Reaction 2

Aminoethanol Derivatives

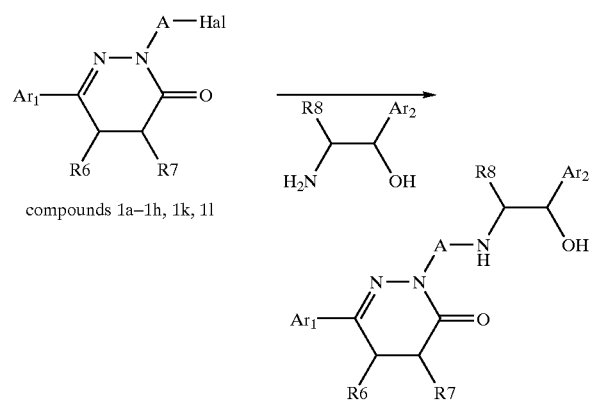

compounds 1a–1h, 1k, 1l

A mixture of 8 mmol of a 2-(ω-halogenalkyl)phthalazinone, 10 mmol of a primary aminoethanol derivative (compounds A, B or C) and 20 mmol of potassium carbonate in 50 ml of dimethylformamide is heated for 1.5 h at 100° C. After cooling to room temperature, a mixture of 100 ml of water and 200 ml of ethyl acetate is added. The organic layer is dried over magnesium sulfate and evaporated. The residue is purified by chromatography (ethyl acetate:triethyl amine/20:1). The aminoethanol derivative is crystallized as a salt with fumaric acid from tetrahydrofurane/diethyl ether.

Reaction 3

Phthalimides (Compounds 2a, 2b or 2c)

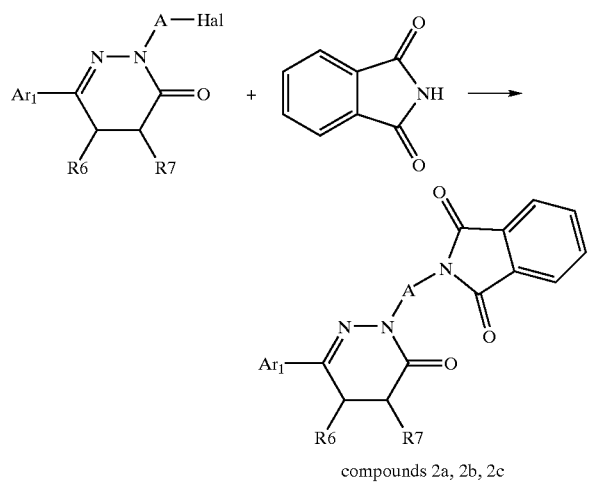

compounds 2a, 2b, 2c 15 mmol of a 2-(ω-halogenalkyl)phthalazinone, 18 mmol of phthalimide and 20 mmol of potassium carbonate in 100 ml of dimethylformamide is heated for 5 h at 110° C. After cooling to room temperature, 300 ml of water and 300 ml of ethyl acetate is added. The organic layer is dried over magnesium sulfate and concentrated under reduced pressure. The compound is crystallized from a suitable solvent.

Reaction 4

2-((ω-aminoalkyl)phthalazinone (compounds 3a, 3b or 3c)

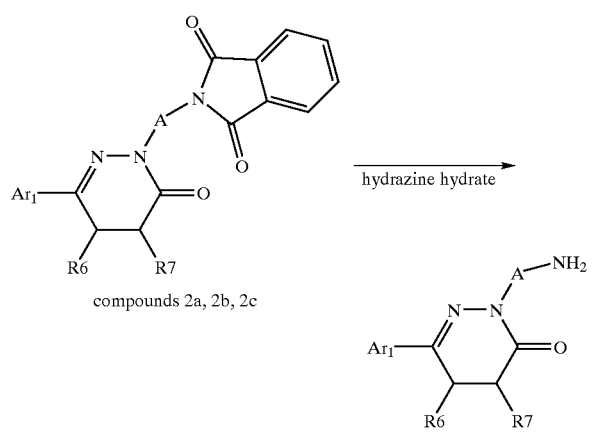

compounds 2a, 2b, 2c compounds 3a, 3b, 3c

A solution of 20 mmol of a phthalimide (compounds 2a, 2b or 2c) and 25 mmol of hydrazine hydrate in 200 ml of ethanol is refluxed for 5 h and subsequently evaporated. The residue is dissolved in ethyl acetate (200 ml) and this solution is washed with aqueous sodium carbonate. After drying over magnesium sulfate, the solvent is evaporated and the residue crystallized from a suitable solvent.

Reaction 5

Aminoethanol Derivatives

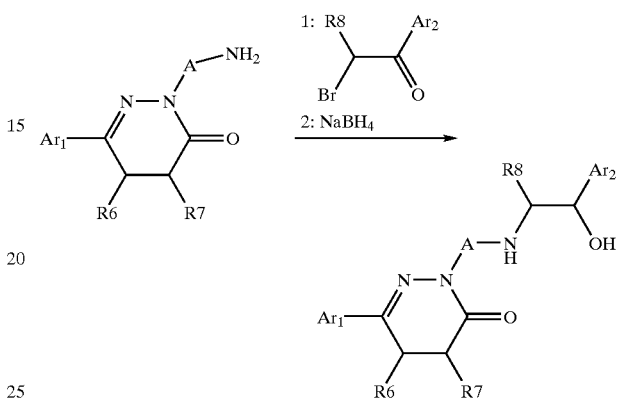

A solution of 6 mmol of a 2-bromoacetophenone derivative (for example: compounds D or E), 5 mmol of an amine (for example: compounds 3a, 3b or 3c) and 10 mmol of diisopropylethylamine in a mixture of 50 ml of tetrahydrofurane and 50 ml of methanol is stirred at room temperature. After 3 h 10 mmol of sodium borohydride is added and the resulting mixture is stirred for another hour and than evaporated. The residue is dissolved in water (100 ml) and this mixture is extracted twice with 200 ml of ethyl acetate. The organic solution is dried over magnesium sulfate and evaporated. The residue is purified by chromatography (ethyl acetate:methanol:triethyl amine/10:2:0.5). The compound is crystallized as a fumarate salt from tetrahydrofurane/diethyl ether.

Reaction 6

Benzylamines

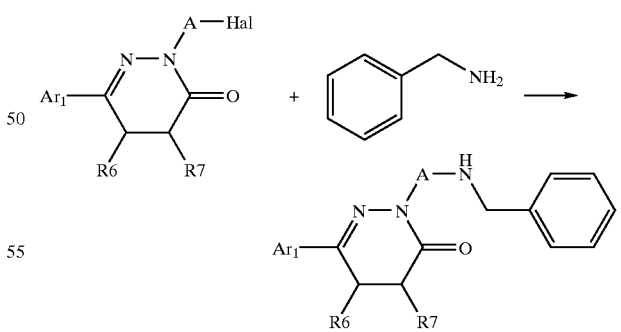

A mixture of 25 mmol of a 2-(ω-halogenalkyl)phthalazinone and 200 mmol of benzylamine is heated at 120° C. for 2 h. After cooling to about 60° C., 200 ml of 2 N hydrobromic acid is added and the resulting mixture is, after cooling to room temperature, extracted twice with 200 ml of dichloromethane. The organic solution is dried over magnesium sulfate and evaporated. The residue is washed with diethyl ether and dried.

Reactions 7/8/9

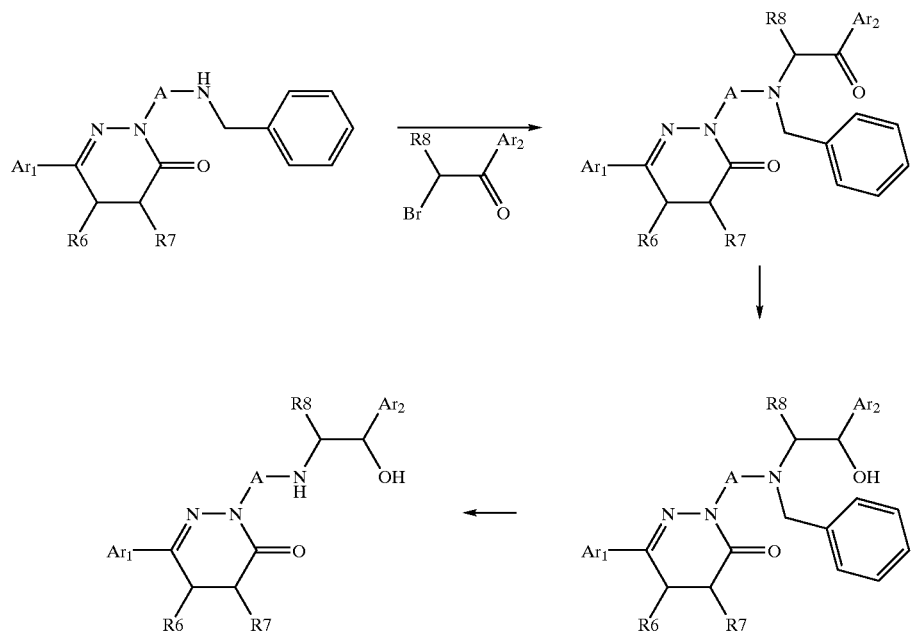

A solution of 10 mmol of a benzylamine (compounds prepared according to REACTION 6), 10 mmol of a 2 bromoacetophenone derivative and 20 mmol of diisopropy-lethylamine in a mixture of 50 ml of tetrahydrofurane and 50 ml of ethanol is stirred for 18 h at room temperature after which 10 mmol of sodium borohydride is added. This mixture is stirred for another 30 min and subsequently evaporated. The residue is dissolved in 200 ml of diethyl ether and this solution is washed with aqueous sodium carbonate. The organic solution is dried over magnesium sulfate and evaporated. The residue is dissolved in ethanol and, after the addition of 0.5 g of 5% Pd/C, treated with a flow of hydrogen. After about 60 min debenzylation is completed (tlc analysis). The catalyst is filtered off, the solvent is evaporated and the residue purified by chromatography on silica (ethyl acetate:triethyl amine/20:1). The aminoethanol derivative is crystallized as a fumarate salt from tetrahydrofurane/diethyl ether.

Reaction 10

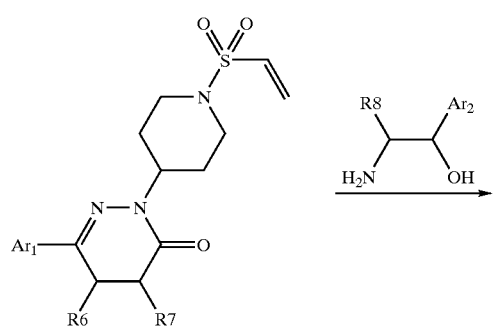

-continued

A mixture of 5 mmol of an ethenesulfonyl derivative (compounds 9a or 12a) and 5 mmol of an aminoethanol derivative (compounds A, B or C) in 50 ml of tetrahydrofuran is stirred for 18 h at RT, after which the solvent is evaporated and the residue purified by chromatography (elution with ethyl acetate containing 5% of triethylamine).

Starting Compounds and Intermediates

1a: (cis)-2-(4-bromo-1-butyl)-4-(3,4-dimethoxyphenyl)-4a,5,6,7,8,8a-hexahydro-2H-phthalazin-1-one Prepared from compound F and 1,4-dibromobutane according to REACTION 1. M. p. oil 1H-NMR(CDCl$_3$): 1.28–2.00 (m, 11H, 7xcyclohexane-H, C—(CH$_2$)$_2$—C); 2.50–2.61 (m, 1H, cyclohexane-H); 2.63–2.73 (m, 1H, cyclohexane-H); 3.00–3.15 (m, 1H, cyclohexane-H); 3.49 (t, J=6.4 Hz, 2H, CH$_2$—Br); 3.72–4.12 (m, 8H, 2×O—CH$_3$, N—CH$_2$); 6.87 (d, J=8.4 Hz, 1H, Ar—H); 7.23 (dd, J=2.1, 8.5 Hz, 1H, Ar—H); 7.47 (d, J=2.0 Hz, 1H, Ar—H).

1b: (cis)-2-(6-bromo-1-hexyl)-4-(3,4-dimethoxyphenyl)-4a,5,6,7,8,8a-hexahydro-2H-phthalazin-1-one Prepared from compound F and 1,6-dibromohexane according to REACTION 1. Crystallized from diethyl ether. M. p. 74–75° C.

1c: (cis)-2-(8-bromo-1-octyl)-4-(3,4-dimethoxyphenyl)-4a,5,6,7,8,8a-hexahydro-2H-phthalazin-1-one Prepared from compound F and 1,8-dibromooctane according to REACTION 1. Crystallized from hexane. M. p. 58–60° C.

1d: (cis)-2-(6-bromo-1-hexyl)-4-(3,4-diethoxyphenyl)-4a,5,6,7,8,8a-hexahydro-2H-phthalazin-1-one Prepared from compound H and 1,6-dibromohexane according to REACTION 1. M. p. 47–51° C.

1e: (cis)-2-(6-bromo-1-hexyl)-4-(3,4-dimethoxyphenyl)-4a,5,8,8a-tetrahydro-2H-phthalazin-1-one Prepared from compound G and 1,6-dibromohexane according to REACTION 1. Crystallized from methanol. M. p. 55–56° C.

1H-NMR(CDCl$_3$): 1.37–2.26 (m, 11H, 3xcyclohexene-H, C—(CH$_2$)$_4$—C); 2.67–2.81 (m, 1H, cyclohexene-H); 2.97–3.07 (m, 1H, cyclohexane-H); 3.28–3.42 (m, 3H, CH$_2$—Br, cyclohexene-H); 3.68–4.06 (m, 8H, 2xO—CH$_3$, N—CH$_2$); 6.88 (d, J=8.5 Hz, 1H, Ar—H); 7.26 (dd, J=2.1, 8.5 Hz, 1H, Ar—H); 7.48 (d, J=2.0 Hz, 1H, Ar—H).

1f: (cis)-2-(4-bromo-1-butyl)-4-(3,4-dimethoxyphenyl)-4a,5,8,8a-tetrahydro-2H-phthalazin-1-one Prepared from compound G and 1,4-dibromobutane according to REACTION 1. Crystallized from methanol. M. p. 102–103° C.

1g: (cis)-2-(5-bromo-1-pentyl)-4-(3,4-dimethoxyphenyl)-4a,5,8,8a-tetrahydro-2H-phthalazin-1-one Prepared from compound G and 1,5-dibromopentane according to REACTION 1. M. p. oil.

1H-NMR(CDCl$_3$): 1.38–2.28 (m, 11H, 3xcyclohexene-H, C—(CH$_2$)$_3$—C); 2.67–2.81 (m, 1H, cyclohexene-H); 2.97–3.07 (m, 1H,cyclohexene-H); 3.28–3.50 (m, 3H, CH$_2$—Br, cyclohexene-H); 3.68–4.08 (m, 9H, 2xO—CH$_3$, N—CH$_2$, cyclohexene-H); 5.60–5.87 (m, 2H, CH=CH); 6.88 (d, J=8.5 Hz, 1H, Ar—H); 7.26 (dd, J=2.0, 8.5 Hz, H, Ar—H); 7.48 (d, J=2.0 Hz, 1H, Ar—H).

1h: (cis)-2-(4-bromo-1-butyl)-4-(2,3-dihydro-7-methoxybenzofuran-2-spiro-1'-cyclopentan-4-yl)-4a,5,8,8a-tetrahydro-2H-phthalazin-1-one Prepared from compound I and 1,4-dibromobutane according to REACTION 1. Crystallized from methanol. M. p. 86–88° C.

1i: (cis)-2-bromoethyl-4-(2,3-dihydro-7-methoxybenzofuran-2-spiro-1'-cyclopentan-4-yl)-4a,5,8,8a-tetrahydro-2H-phthalazin-1-one A solution 1.92 g of Br$_2$ in CH$_2$Cl$_2$ is added to a solution of 3.1 g of triphenylphosphine in CH$_2$Cl$_2$ at 0° C. followed by the addition of a solution of 4.6 g of compound L in CH$_2$Cl$_2$. The resulting solution is stirred for 2 h at room temperature and subsequently washed with diluted hydrochloric acid (2×) and aqueous sodium carbonate. Crystallization from methanol (2×). M. p. 143–145° C.

1j: (cis)-2-{4-(2-bromoethyl)phenyl}-4-(3,4-dimethoxyphenyl)-4a,5,8,8a-tetrahydro-2H-phthalazin-1-one Prepared from M as described for intermediate 1i. Crystallized from methanol. M. p. 126–127° C.

1k: 2-(6-bromo-1-hexyl)-4-(3,4-dimethoxyphenyl)-2H-phthalazin-1-one

Prepared from compound J and 1,6-dibromohexane according to REACTION 1. Crystallized from a mixture of ethyl acetate and hexane. M. p. 83–84° C.

1l: 2-(6-bromo-1-hexyl)-4-(3-methoxy-4-difluoromethoxyphenyl)-2H-pyridazin-1-one Prepared from compound K and 1,6-dibromohexane according to REACTION 1. Crystallized from diethyl ether. M. p. 69–70° C.

2a: (cis)-N-[6-{4-(3,4-dimethoxyphenyl)-1-oxo-4a,5,8,8a-tetrahydro-2H-phthalazin-2-yl}hexyl]-phthalimide Prepared from compound 1e according to REACTION 3. Crystallized from methanol. M. p. 104–105° C.

2b: (cis)-N-[4-{4-(3,4-dimethoxyphenyl)-1-oxo-4a,5,8,8a-tetrahydro-2H-phthalazin-2-yl}butyl]-phthalimide Prepared from compound 1f according to REACTION 3. Crystallized from methanol. M. p. 139–140° C.

2c: (cis)-N-[5-{4-(3,4-dimethoxyphenyl)-1-oxo-4a,5,8,8a-tetrahydro-2H-phthalazin-2-yl}pentyl]-phthalimide Prepared from compound 1g according to REACTION 3. Crystallized from diethyl ether. M. p. 126–129° C.

3a: (cis)-2-(6-amino-1-hexyl)-4-(3,4-dimethoxyphenyl)-4a,5,8,8a-tetrahydro-2H-phthalazin-1-one Prepared from compound 2a according to REACTION 4. Crystallized from tetrahydrofurane/diethyl ether as a fumarate salt. M. p. 141–143° C.

3b: (cis)-2-(4-amino-1-butyl)-4-(3,4-dimethoxyphenyl)-4a,5,8,8a-tetrahydro-2H-phthalazin-1-one Prepared from compound 2b according to REACTION 4. Crystallized from diethyl ether. M. p. 108–109° C.

3c: (cis)-2-(5-amino-1-pentyl)-4-(3,4-dimethoxyphenyl)-4a,5,8,8a-tetrahydro-2H-phthalazin-1-one Prepared from compound 2c according to REACTION 4. Crystallized from diethyl ether. M. p. 88–89.

4a: (cis)-2-(6-benzylamino-1-hexyl)-4-(3,4-dimethoxyphenyl)-4a,5,6,7,8,8a-hexahydro-2H-phthalazin-1-one HBr Prepared from compound 1b according to REACTION 6. M. p. 117–119° C.

5a: (4aS,8aR)-2-[1-(4-amino-butanoyl)-piperidin-4-yl]-4-(3,4-dimethoxy-phenyl)-4a,5,8,8a-tetrahydro-2H-phthalazin-1-one trifluoroacetate 15 mmol of compound 5b is dissolved in 20 ml of trifluoroacetic acid and the solution is left at RT for 30 min after which it is evaporated. The residue solidifies on treating with diethyl ether. M. p. 175–178° C.

5b: (4-{4-[(4aS,8aR)-4-(3,4-dimethoxy-phenyl)-1-oxo-4a,5,8,8a-tetrahydro1H-phthalazin-2-yl]-piperidin-1-yl}-4-oxo-butyl)-carbamic acid tert butyl ester To a solution of 20 mmol of compound 5c and 25 mmol of (4-Oxo-pentyl)-carbamic acid tert-butyl ester in 100 ml of dichloromethane, 25 mmol of (3-dimethylamino-propyl)-ethyl-carbodiimide hydrochloride is added and the resulting mixture is stirred at RT. After 18 h the solution is washed successively with diluted hydrochloric acid and aqueous sodium carbonate and then dried over magnesium sulfate. After evaporating the solvent, the compound is crystallised from hexane. M. p. 79–83° C.

5c: (4aS,8aR)-4-(3,4-Dimethoxy-phenyl)-2-piperidin-4-yl-4a,5,8,8a-tetrahydro-2H-phthalazin-1-one A solution of 50 mmol of compound 5d in 150 ml of dichloromethane is washed with a saturated solution of sodium bicarbonate, dried over magnesium sulfate and evaporated. The residue is washed with diethyl ether and dried. M. p. 260° C. (with decomposition).

5d: (4aS,8aR)-4-(3,4-Dimethoxy-phonyl)-2-piperidin-4-yl-4a,5,8,8a-tetrahydro-2H-phthalazin-1-one hydrochloride A solution of 50 mmol of the salt of (S)-(-)-α-methylbenzylamine and (cis)-2-(3,4-dimethoxybenzoyl)-1,2,3,6-tetrahydrobenzoic acid (compound N), 55 mmol of piperidin-4-yl-hydrazine dihydrochloride and 100 mmol of triethylamine in 150 ml of 1-propanol is refluxed for 18 h. After cooling to RT, the precipitate is filtered off and dried. M. p. 285–288° C.

5e: Piperidin-4-yl-hydrazine dihydrochloride

A mixture of 0.1 mole of 4-(N'-tert-butoxycarbonyl-hydrazino)-piperidine-1-carboxylic acid tert-butyl ester (compound 5f) and 150 ml of concentrated hydrochloric acid is heated at 90° C. for 60 min after which the clear solution is evaporated. The residue is washed with tetrahydrofurane, filtered off and dried under vacuum. M. p. 256–259° C.

5f: 4-(N'-tert-Butoxycarbonyl-hydrazino)-piperidine-1-carboxylic acid tert-butyl ester 150 ml of a solution of borohydride in tertahydrofurane (1.0 mol/l) is slowly added to a solution of 0.12 mole of 4-(tert-butoxycarbonyl-hydrazono)-piperidine-1-carboxylic acid tert-butyl ester (compound 5 g) in 100 ml of dry tetrahydrofurane. After complete addition, the mixture is stirred for another 30 min after which a 100 ml of water is added to destroy the excess of borohydride. Subsequently the tetrahydrofurane is evaporated and the resulting aqeous solution extracted with diethyl ether. After drying the solvent over magnesium sulfate, the ether is evaporated. M. p. 112–115° C.

5g: 4-(tert-Butoxycarbonyl-hydrazono)-piperidine-1-carboxylic acid tert-butyl ester A mixture of 0.15 mole of 4-oxo-piperidine-1-carboxylic acid tert-butyl ester (commercially available) and 0.15 mole of tert-butylcarbazate in 250 ml of hexane is stirred for 18 h at RT. The precipitate is filtered off and dried under vacuum. M. p. 172–174° C.

6a: (4aS,8aR)-2-[4-(4-Bromo-butoxy)-phenyl]-4-(3,4-dimethoxy-phenyl)-4a,5,8,8a-tetrahydro-2H-phthalazin-1-one A mixture of 10 mmol of compound 6b, 50 mmol of 1,4-dibromobutane and 40 mmol of potassium carbonate in 50 ml of dimethylformamide is stirred for 18 h at RT, after which the mixture is poured into 200 ml of water. After extraction with diethyl ether, the compound is purified by chromatography (ethyl acetate:hexane/1;5). Crystallised from hexane at −20° C. M. p. 38–43° C.

6b: (4aS,8aR)-4-(3,4-Dimethoxy-phenyl)-2-(4-hydroxy-phenyl)-4a,5,8,8a-tetrahydro-2H-phthalazin-1-one A mixture of 20 mmol of compound 6c, 50 ml of ethanethiol and 20 ml of borontrifluoride etherate is left at RT for 40 h. After the addition of 200 ml of a saturated solution of sodium bicarbonate, the mixture is extracted with ethyl acetate. The organic solution is dried over magnesium sulfate and evaporated. The compound is crystallised from diethyl ether. M. p. 111–112° C.

6c: (4aS,8aR)-2-(4Benzyloxy-phenyl)-4-(3,4-dimethoxy-phenyl)-4a,5,8,8a-tetrahydro-2H-phthalazin-1-one A solution of 50 mmol of compound 6d and 50 mmol of 4-benzyloxyphenylhydrazine hydrochloride in 100 ml of pyridine is refluxed for 8 h and subsequently evaporated. The residue is dissolved in ethyl acetate and the solution is washed successively with diluted hydrochloric acid and aqueous sodium carbonate and then dried over magnesium sulfate. After evaporating the solvent, the compound is crystallised from methanol. M. p. 104–105° C.

6d: (1R,6S)-6-[1-(3,4-dimethoxy-phenyl)-methanoyl]-1,2,3,6-tetrahydrobenzoic acid A solution of 50 mmol of compound 6e in 150 ml of dichloromethane is washed successively with 1 N sulfuric acid and water (twice). The solution is dried over magnesium sulfate and evaporated. The residue is crystallised from diethyl ether. M. p. 110–112° C.

6e: (1R,2S)-2-(3,4-Dimethoxy-phenyl)-methanoyl)-1,2,3,6-tetrahydrobenzoic acid (−)-α-methylbenzylamine salt A mixture of 10 mmol of compound N and 5 mmol of L-α-methylbenzylamine in 100 ml of ethyl acetate is stirred for 18 h after which the precipitate is filtered off and dried.

7a: (4aS,8aR)-2-[4-(4-Bromo-butoxy)-benzyl]-4-(3,4-dimethoxy-phenyl)-4a,5,8,8a-tetrahydro-2H-phthalazin-1-one Prepared from compound 7b and 1,4-dibromobutane as described for compound 6a. M. p. 42–46° C.

7b: (4aS,8aR)-4-(3,4-Dimethoxy-phonyl)-2-(4-hydroxy-benzyl)-4a,5,8,8a-tetrahydro-2H-phthalazin-1-one Prepared from 4-hydroxybenzylhydrazine hydrochloride and compound 6d as described for compound 6c. Crystallised from diethyl ether. M. p. 189–190° C.

8a: (4aS,8aR)-2-[4-(2-Bromo-ethoxy)-phenyl]-4-(3,4-dimethoxy-phenyl)-4a,5,8,8a-tetrahydro-2H-phthalazin-1-one Prepared from compound 6b and 1,2-dibromoethane as described for compound 6a. M. p. 40–45° C.

9a: (4aS,8aR)-4-(3,4-Dimethoxy-phenyl)-2-[1-(2-ethenesulfonyl-ethyl)-piperidin-4-yl]-4a,5,8,8a-tetrahydro-2H-phthalazin-1-one A solution of 10 mmol of compound 5c, 10 mmol of 1-bromo-2-(2-bromo-ethanesulfonyl)-ethane and 30 mmol of potassium carbonate in 30 ml of dimethylformamide is stirred at RT. After 18 h, the mixture is poured into water (150 ml) and subsequently extracted with ethyl acetate. Crystallisation from diethyl ether. M. p. 165–166° C.

10a: 4-[(4aS,8aR)-4-(3,4-Dimethoxy-phenyl)-1-oxo-4a,5,8,8a-tetrahydro-1H-phthalazin-2-yl]-piperidine-1-carbothioic acid (4-amino-butyl)-amide trifluoroacetate Prepared from compound 10b as described for compound 5a. M. p. 125–128° C.

10b: {4-[(1-{4-[(4aS,8aR)-4-(3,4-Dimethoxy-phenyl)-1-oxo-4a,5,8,8a-tetrahydro-1-phthalazin-2-yl]-piperidin-1-yl}-methanethioyl)-amino]-butyl}-carbamic acid tert butyl ester A solution of 10 mmol of (4-Isothiocyanato-butyl)-carbamic acid tert butyl ester and 10 mmol of compound 5c in 100 ml of dichloromethane is stirred for 18 h at RT, successively washed with diluted hydrochloric acid and aqueous sodium carbonate and subsequently dried over magnesium sulfate and evaporated. Crystallised from a mixture of ethyl acetate and hexane. M. p. 118–121° C.

11a: (4aS,8aR)-2-[1-(2-Chloro-ethanoyl)-piperidin-4-yl]-4-(3,4-diethoxy-phenyl)-4a,5,8,8a-tetrahydro-2H-phthalazin-1-one A solution of 12 mmol of chloroacetylchloride in 20 ml of dichloromethane is added at 0° C. to a mixture of 12 mmol of compound 11b and 40 mmol of triethylamine in 50 ml of dichloromethane. The resulting mixture is stirred for 60 min at RT and subsequently washed with diluted hydrochloric acid and aqueous sodium carbonate. After drying the solution over magnesium sulfate, the solvent is evaporated and the residue purified by chromatography (ethyl acetate:petroleum ether (60–80° C.)/2:1). M. p. 135–136° C.

11b: (4aS,8aR)-4-(3,4-Diethoxy-phenyl)-2-piperidin-4-yl-4a,5,8,8a-tetrahydro-2H-phthalazin-1-one hydrochloride Prepared from the salt of (S)-(−)-α-methylbenzylamine, (cis)-2-(3,4-diethoxybenzoyl)-1,2,3,6-tetrahydrobenzoic acid (compound P) and piperidin-4-yl-hydrazine dihydrochloride in 2-propanol as described for compound 5d. M. p. 248–250° C.

12a: (4aS,8aR)-4-(3,4-Dimethoxy-phenyl)-2-(1-ethenesulfonyl-piperidin-4-yl)-4a,5,8,8a-tetrahydro-2H-phthalazin-1-one A solution of 20 mmol of 2-chloroethylsulfonylchloride in 20 ml of dichloromethane is added to a solution of 15 mmol of compound 5c and 25 ml of diisopropylethylamine in 50 ml of dichloromethane. The resulting mixture is stirred at RT for 18 h, after which it is washed first with diluted hydrochloric acid and then with a saturated solution of sodium bicarbonate. After drying over magnesium sulfate and evaporating the solvent, the compound is crystallised from diethyl ether. M. p. 89–90° C.

13a: (4aS,8aR)-2-[1-((S)-2-Amino-propanoyl)-piperidin-4-yl]-4-(3,4-dimethoxy-phenyl)-4a,5,8,8a-tetrahydro-2H-phthalazin-1-one Prepared from compound 13b as described for compound 5a. After evaporating the trifluoroacetic acid, the residue is partitioned between aqueous sodium carbonate and dichloromethane. The organic solution is dried over magnesium sulfate and evaporated. The residue is crystallised from diethyl ether. M. p. 101–103° C.

13b: 1-tert-Butyl-3-((S)-2-{4-[(4aS,8aR)-4-(3,4-dimethoxy-phenyl)-1-oxo-4a,5,8,8a-tetrahydro-1H-phthalazin-2-yl]-piperidin-1-yl}-1-methyl-2-oxo-ethyl)-urea Prepared from compound 5c and (R)-2-(3-tert-butyl-ureido)-propionic acid (N-boc-L-alanine) as described for compound 5b. M. p. 153–154° C.

14a. (4aS,8aR)-2-{1-[3-(2-Amino-ethylsulfanyl)-propanoyl]-piperidin-4-yl}-4-(3,4-dimethoxy-phenyl)-4a,5,8,8a-tetrahydro-2H-phthalazin-1-one Prepared from compound 14b as described for compound 5c. After evaporating the trifluoroacetic acid, the residue is partitioned between a bicarbonate solution and dichloromethane. The dichloromethane solution is dried over magnesium sulfate and evaporated. Crystallised from ethyl acetate/hexane. M. p. 137–139° C.

14b. [2-(3-{4-[(4aS,8aR)-4-(3,4-Dimethoxy-phenyl)-1-oxo-4a,5,8,8a-tetrahydro-1H-phthalazin-2-yl]-piperidin-1-yl}-3-oxo-propylsulfanyl)-etyl]-carbamic acid tert butyl ester Prepared from 12 mmol of 3-(2-tert-butoxycarbonylamino-ethylsulfanyl)-propionic acid and 10 mmol of compound 5c as described for compound 5b. M. p. 132–134° C.

15a. (4aS,8aR)-2-{1-[3-(2-Amino-ethanesulfonyl)-propanoyl]-piperidin-4-yl}-4-(3,4-dimethoxy-phenyl)-4a,5,8,8a-tetrahydro-2H-phthalazin-1-one hydrochloride 20 mmol of 3-chloroperbenzoic acid is added to a solution of 10 mmol of compound 14a in 50 ml of dichioromethane. The resulting mixture is stirred for 30 min at RT and subsequently washed with aqueous sodium carbonate. After drying over magnesium sulfate, a solution of hydrochloric acid in diethyl ether is added to the dichloromethane solution. The precipitate is filtered off and dried. M. p. 149–150° C.

16a. (4aS,8aR)-2-[1-(6-Amino-hexyl)-piperidin-4-yl]-4-(3,4-dimethoxy-phenyl)-4a,5,8,8a-tetrahydro-2H-phthalazin-1-one hydrochloride Prepared from compound 16b as described in REACTION 4. Crystallised from ethyl acetate as the hydrochloride. M. p. 176–177° C.

16b. 2-(6-{4-[(4aS,8aR)-4-(3,4-Dimethoxy-phenyl)-1-oxo-4a,5,8,8a-tetrahydro-1H-phthalazin-2-yl]-piperidin-1-yl}-hexyl)-isoindole-1,3-dione A mixture of 6 mmol of 2-(6-bromo-hexyl)-isoindole-1,3-dione, 6 mmol of compound 5c and 3 g of potassium carbonate in 50 ml of dimethylformamide is stirred for 18 h at RT. After evaporating the solvent, the residue is partitioned between water and ethyl acetate. The organic layer is dried over magnesium sulfate and evaporated. The residue is purified by chromatography (ethyl acetate:hexane/4:1). M. p. 39–44° C.

A: 2-amino-1-(4-amino-3,5-dichlorophenyl)ethanol

Prepared as described in J. Keck, G. Kruger, K. Noll and H. Machleidt; Arzneim.-Forsch. (Drug Res.) 22, 861–869 (1972).

B: 2-amino-1-(4-amino-3-chloro-5-trifluoromethylphenyl)ethanol

Prepared as described in G. Krülger, J. Keck, K. Noll and H. Pieper; Arzneim.-Forsch./Drug Res. 34, 1612–1624 (1984).

C: 2-amino-1-(4-hydroxy-3-hydroxymethylphenyl)ethanol

Prepared as described in D. T. Cullin, D. Hartley, L. H. C. Lunts, J. C. Press, A. C. Ritchie and P. Toon; J. Med. Chem., 13, 674–680 (1970).

D: 4'-amino-3'-chloro-5'-cyano-2-bromoacetophenone

Prepared as described in G. Krüger, J. Keck, K. Noll and H. Pieper; Arzneim.-Forsch./Drug Res. 34, 1612–1624 (1984).

E: 4'-amino-3'-cyano-2-bromoacetophenone

Prepared as described in G. Krüger, J. Keck, K. Noll and H. Pieper; Arzneim.-Forsch./Drug Res. 34, 1612–1624 (1984).

F: 4-(3,4-dimethoxyphenyl)-4a,5,6,7,8,8a-hexahydro-2H-phthalazin-1-one

Prepared as described in example 1 of WO98/31674.

G: 4-(3,4-dimethoxyphenyl)-4a,5,8,8a-tetrahydro-2H-phthalazin-1-one

Prepared as described in example 3 of WO98/31674.

H: 4-(3,4-diethoxyphenyl)-4a,5,6,7,8,8a-hexahydro-2H-phthalazin-1-one

Prepared as described in example 7 of WO98/31674.

I: (cis)-4-(2,3-dihydro-7-methoxybenzofuran-2-spiro-1'-cyclopentan-4-yl)-4a,5,8,8a-tetra-hydro-2H-phthalazin-1-one Prepared as described in example 4 of WO99/31090.

J: 4-(3,4-dimethoxyphenyl)-2H-phthalazin-1-one

Prepared as described in example B of EP0934933.

K: 4-(4-Difluoromethoxy-3-methoxyphenyl)-2H-pyridazin-1-one

Prepared as described in example 4 of EP0163965.

L: (cis)-4-(2,3-dihydro-7-methoxybenzofuran-2-spiro-1'-cyclopentan-4-yl)-2-hydroxyethyl-4a,5,8,8a-tetrahydro-2H-phthalazin-1-one Prepared as described in example 17 of WO99/31090.

M: (cis)-4-(3,4-dimethoxyphenyl)-2-{4-(2-hydroxyethyl)phonyl}-4a,5,8,8a-tetrahydro-2H-phthalazin-1-one Prepared as described in example 70 of WO98/31674.

N. (cis)-2-(3,4-Dimethoxybenzoyl)-1,2,3,6-tetrahydrobenzoic acid

Prepared as described in WO98/31674.

O. 1-(4-Amino-3,5-dichloro-phenyl)-2-bromo-ethanone

Prepared as described by J. Keck, G. Krüger, K. Noll and H. Machleidt; Arzneim.-Forsch. (Drug Res.) 22, 861–869 (1972).

P. (cis)-2-(3,4-diethoxybenzoyl)-1,2,3,6-tetrahydrobenzoic acid

Prepared analogously as described for compound N.

Commercial Applicability

β-Sympathomimetics (β2-adrenoreceptor agonists) represent the preferred drugs for the acute relief of bronchospasm in patients with bronchial asthma (Nelson H S, β-Adrenergic bronchodilators. The New England of Medicine 333: 499–506, 1995). Although the major action of β-sympathomimetics on the airways is relaxation of airway smooth muscle, inhibitory effects on inflammatory cells (e.g. mast cells, eosinophils, neutrophils, macrophages and T-lymphocytes) in vitro have been reported (Barnes P J, Effect of beta-agonists on inflammatory cells. Journal of Allergy and Clinical Immunology 104: S10–S17, 1999). Despite the inhibitory effects on inflammatory cells in vitro, however, β-sympathomimetics do not appear to reduce the chronic inflammation of asthma. Desensitization to the action of β-sympathomimetics is more readily seen in inflammatory cells than in airway smooth muscle cells and may account for this discrepancy. It has been suggested that an accelerated degradation of cAMP by phosphodiesterase 4 (PDE4) could be an explanation for this kind of desensitization (Giembycz M A, Phosphodiesterase 4 and tolerance to β2-adrenoceptor agonists in asthma. TiPS 17: 331–336, 1996). Therefore, the combined action of one molecule to inhibit PDE4 activity and to activate the β2-adrenoceptor is claimed to counteract the development of tolerance to β2-adrenoceptor agonists in vivo. In addition, such molecules with a combined mode of action will maintain the well-known anti-inflammatory potential of PDE4 inhibitors (Torphy T J, Phosphodiesterase isozymes—molecular targets for novel antiasthma agents. Am J Respir Crit Care Med 157: 351–370, 1998), or even make the PDE4 inhibiting component by the β2-adrenoceptor agonistic component (more) effective under conditions where a PDE4 inhibitor requires an additional cAMP trigger for its action. One example for the latter possibility is the human eosinophil which upon stimulation by complement C5a does not respond to PDE4 inhibitors alone, but is inhibited in a highly synergistic fashion by the combined use of PDE4 inhibitors and a β2-adrenoceptor agonist like salbutamol (Hatzelmann A, Tenor H and Schudt C, Differential effects of non-selective and selective phosphodiesterase inhibitors on human eosinophil function. Brit J Pharmacol 114: 821–831, 1995).

The compounds according to the invention have valuable pharmacological properties which make them commercially utilizable. As compounds providing selective PDE4 inhibition combined with β2-adrenoceptor agonist activity they are suitable on the one hand as bronchial therapeutics (for the treatment of airway obstructions on account of their dilating but also on account of their respiratory rate- or respiratory drive-increasing action), but on the other hand especially for the treatment of disorders, in particular of inflammatory nature, e.g. of the airways, of the skin, of the central nervous system, of the intestine, of the eyes and of the joints, which are mediated by mediators such as histamine, PAF (platelet-activating factor), arachidonic acid metabolites such as leukotrienes and prostaglandins, cytokines, interleukins, chemokines, alpha-, beta- and gamma-interferon, tumor necrosis factor (TNF) or oxygen radicals and proteases.

On account of their PDE4-inhibiting properties, the compounds according to the invention can be employed in human and veterinary medicine and therapeutics, where they can be used, for example, for the treatment and prophylaxis of the following illnesses: acute and chronic (in particular inflammatory and allergen-induced) airway disorders of various origins (bronchitis, allergic bronchitis, bronchial asthma, emphysema, COPD); dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), graft-versus-host reactions, transplant rejection reactions, symptoms of shock [septic shock, endotoxin shock, gram-negative sepsis, toxic shock syndrome and ARDS (adult respiratory distress syndrome)], and generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones. In addition, the compounds according to the invention can be employed for the treatment of diabetes insipidus and disorders in connection with disturbances of brain metabolism, such as, for example, cerebral senility, senile dementia (Alzheimer's dementia), multiinfarct dementia or alternatively disorders of the CNS, such as, for example, depressions, arteriosclerotic dementia, Alzheimer's disease or multiple sclerosis.

A further subject of the invention is a process for the treatment of mammals, including man, which are suffering from one of the above-mentioned illnesses. The process comprises administering to the sick mammal a therapeutically efficacious and pharmacologically tolerable amount of one or more of the compounds according to the invention.

The invention further relates to the compounds according to the invention for use in the treatment of mammals, including man, which are suffering from one of the above-mentioned illnesses. The process comprises administering to the sick mammal a therapeutically efficacious and pharmacologically tolerable amount of one or more of the compounds according to the invention.

The invention further relates to the compounds according to the invention for use in the treatment and/or prophylaxis of illnesses, in particular the illnesses mentioned.

The invention likewise relates to the use of the compounds according to the invention for the production of medicaments which are employed for the treatment and/or prophylaxis of the illnesses mentioned.

Medicaments for the treatment and/or prophylaxis of the illnesses mentioned, which contain one or more of the compounds according to the invention, are furthermore a subject of the invention.

A further subject of the invention is a commercial product, consisting of a customary secondary pack, a primary pack containing the medicament (for example an inhaler or a blister pack) and, optionally, a pack insert, the medicament exhibiting simultaneously antagonistic action against cyclic nucleotide phosphodiesterases of type 4 (PDE4) and agonistic action on β2-adrenoreceptors leading to the attenuation of the symptoms of illnesses which are connected with cyclic nucleotide phosphodiesterases of type 4 and β2-adrenoreceptors, and the suitability of the medicament for the prophylaxis or treatment of illnesses which are connected with cyclic nucleotide phosphodiesterases of the type 4 and β2-adrenoreceptors being indicated on the secondary pack and/or on the pack insert of the commercial product, and the medicament containing one or more compounds of the formula I according to the invention. The secondary pack, the primary pack containing the medicament and the pack insert otherwise comply with what would be regarded as standard to the person skilled in the art for medicaments of this type.

The medicaments are prepared by processes which are known per se and familiar to the person skilled in the art. As medicaments, the compounds according to the invention (=active compounds) are either employed as such, or preferably in combination with suitable pharmaceutical excipients, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers, permeation promoters or complex formers.

For the treatment of disorders of the respiratory tract, the compounds according to the invention are preferably also administered by inhalation.

Aerosol particles in solid, liquid or mixed composition with a diameter from 0.5 to 10 μm, preferably 2 to 6 μm, are preferably used, if the compounds of the invention are administered by inhalation. The aerosol generation can be effected, for example, through pressure driven jet nebulizers or ultrasonic nebulizers, preferably however through propellant driven metered dose aerosols or through propellant free use of micronized active substances out of inhalation capsules.

Dependant on the used inhalation system the inhalation preparations contain additional to the active substance(s)

further required excipients, such as propellants (for example Frigen in metered dose inhalers), surfactants, emulgators, stabilisators, preservatives, flavouring agents or fillers (for example lactose in powder inhalers).

For the purpose of inhalation a variety of devices are available with which aerosols with an optimal particle size can be generated and administered in a manner highly adapted to the patients. Beside the use of adapters (Spacer, Expander) and pear-shaped containers (for example Nebulator®, Volumatic®), as well as automatic spray burst shutter (Autohaler®) for metered dose inhalers, in particular in the field the powder inhalers there exists a variety of technical solutions (for example Diskhaler®, Rotadisk®, Turbohaler® or the inhaler described in EP 0 505321) with which an optimal administration of the active substance(s) can be achieved.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. Dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

Biological Investigations

In the investigation of the combined action of the compounds (PDE4 inhibition and β2-adrenoceptor agonism) at the cellular level, the activation of inflammatory cells has particular importance. As an example, the complement C5a-induced superoxide production of eosinophilic granulocytes may be mentioned, which can be measured as luminol-potentiated chemiluminescence (Hatzelmann A, Tenor H and Schudt C, Differential effects of non-selective and selective phosphodiesterase inhibitors on human eosinophil function. Brit J Pharmacol 114: 821–831, 1995). In this experimental setting PDE4 inhibitors by themselves are ineffective unless β2-adrenoceptors are stimulated simultaneously.

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21–40, "The Handbook of Immunopharmacology", Academic Press, 1996), and its inhibition leads to an increase of the intracellular cAMP concentration and thus to the inhibition of cellular activation (J E Souness et al., Immunopharmacology 47:127–162, 2000).

The antiinflammatory potential of PDE4 inhibitors in vivo in various animal models has been described (M M Teixeira, TIPS 18: 164–170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682–690, 1991) or eosinophilic (A Hatzelmann et al., Brit J Pharmacol 114: 821–831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221–231, 1997, and Pulmonary Pharmacol Therap 12: 377–386, 1999). In addition, the immunomodulatory potential of PDE4 inhibitors is evident from the inhibition of T-cell responses like cytokine synthesis or proliferation (D M Essayan, Biochem Pharmacol 57: 965–973, 1999). Substances which inhibit the secretion of the aforementioned proinflammatory mediators are those which inhibit PDE4. The antiinflammatory action of compounds having a PDE4 inhibitory component may be enhanced by the β2-adrenoceptor agonistic component in additive or synergistic fashion.

Method for Measuring Inhibition of PDE4 Activity

PDE4 activity was determined as described by Thompson et al. (Adv Cycl Nucl Res 10: 69–92, 1979) with some modifications (Bauer and Schwabe, Naunyn-Schmiedeberg's Arch Pharmacol 311: 193–198, 1980). At a final assay volume of 200 μl (96well microtiter plates) the assay mixture contained 20 mM Tris-HCl (pH 7.4), 5 mM $MgCl_2$, 0.5 μM cAMP, [$^3$H]cAMP (about 30,000 cpm/assay), the test compound and an aliquot of cytosol from human neutrophils which mainly contains PDE4 activity as described by Schudt et al. (Naunyn-Schmiedeberg's Arch Pharmacol 344: 682–690, 1991); the PDE3-specific inhibitor Motapizone (1 μM) was included to suppress PDE3 activity originating from contaminating platelets.

For (some of) the examples 1–19 stock solutions of the compounds (2 mmol/l) were prepared in DMSO and diluted 1:100 (v/v) in the Tris-HCl buffer mentioned above; appropriate dilutions were prepared in 1% (v/v) DMSO/Tris-HCl which were diluted 1:2 (v/v) in the assays to obtain the final concentrations of the inhibitors at a DMSO concentration of 0.5% (v/v) which by itself did not affect PDE activity.

To minimize problems with the solubility of the compounds, starting from example 20 serial dilutions of the compounds were prepared directly in DMSO and further diluted 1:100 (v/v) in the assays to obtain now the final concentrations of the inhibitors at a DMSO concentration of 1% (v/v) which by itself only slightly affected PDE4 activity.

After preincubation for 5 min at 37° C., the reaction was started by the addition of substrate (cAMP) and the assays were incubated for further 15 min at 37° C. 50 μl of 0.2 N HCl was added to stop the reaction and the assays were left on ice for about 10 min. Following incubation with 25 μg 5'-nucleotidase (Crotalus atrox snake venom) for 10 min at 37° C., the assays were loaded on QAE Sephadex A-25 (1 ml bed volume). The columns were eluted with 2 ml of 30 mM ammonium formiate (pH 6.0) and the eluate was counted for radioactivity. Results were corrected for blank values (measured in the presence of denatured protein) which were below 5% of total radioactivity. The amount of cyclic nucleotides hydrolyzed did not exceed 30% of the original substrate concentration. The $IC_{50}$-values for the compounds according to the invention for the inhibition of the PDE4 activity were determined from the concentration-inhibition curves by nonlinear-regression.

The PDE4-inhibitory values determined for the compounds according to the invention [inhibitory concentration as $-\log IC_{50}$ (mol/l)] follow from Table A below, in which the numbers of the compounds correspond to the numbers of the examples.

b) β2-Adrenoceptor Agonistic Activity in Isolated Guinea-pig Trachea

Male guinea-pigs (350–450 g) were killed by a sharp blow on the head and exsanguination, after that the trachea was removed. After clearing off adhering tissue the trachea was cut into single rings which were tied together forming up to six 4- to 5-ring chains which were suspended in 10-ml organ baths containing Krebs buffer of the following composition (mM): NaCl 118, KCl 5.2, $CaCl_2$ 1.9, $MgSO_4$ 0.56, $NaH_2PO_4$ 0.8, $NaHCO_3$ 25.0, and glucose 11.1, maintained at 37° C. and continuously aerated with a mixture of 95% $O_2$ and 5% $CO_2$. The end of the chain was tied at the bottom of the tissue bath and connected to a force-displacement transducer (Type K-30, Hugo Sachs Elektronik, Germany) for the recording of isometric tension changes and then placed under 1.5 to 2 g of tension. After a 60 min equilibration period, during which time the preparations were repeatedly washed and the spontaneous contraction plateaud, each tracheal preparation was pre-treated with $3 \times 10^{-7}$ M of RP 73401 for total inhibition of PDE4, which caused relaxation of the tissue between 30 and 40% of maximum (Harris et al., 1989, JPET 251: 199–206). After stabilization of the relaxant response to RP 73401, the test drugs were administered in a cumulative manner (factor 3), each concentration remaining in contact with the trachea until the contractile response reached a plateau, before addition of the next higher concentration. At the end of the test drug administration, which caused maximal relaxation the tissue (verified in control experiments for each test drug by additional administration of $10^{-6}$ M (−)-isoprenaline), a high concentration of the β-adrenoceptor antagonist, dl-sotalol ($3–6 \times 10^{-4}$ M), was additionally given to assess whether the relaxant response of the trachea to test compound was due to $\beta_2$-adrenoceptor stimulation. dl-Sotalol nearly completely reversed the relaxation amplitude to the test compounds and was taken as evidence for their $\beta_2$-adrenoceptor agonistic property. The relaxant response to test compound was expressed as percent determined between the relaxant amplitude after that reached by RP 73401 (0%) and the maximal relaxation obtained prior to dl-sotalol administration (100%). $EC_{50}$ values for a half-maximal relaxation of the tissue by test compound were graphically interpolated from 12 to 16 individual concentration-response curve. The $-\log EC_{50}$ values (mol/l) thus obtained were taken as a measure for $\beta_2$-adrenoceptor agonistic activity of the test compounds.

The $-\log EC_{50}$ values (mol/l) for the compounds according to the invention follow from the Table A below, in which the numbers of the compounds correspond to the numbers of the examples.

c) Inhibition of C5a-stimulated Chemiluminescence in Human Eosinophils

Eosinophils were purified essentially as described in detail elsewhere (Hatzelmann A, Tenor H and Schudt C, Differential effects of non-selective and selective phosphodiesterase inhibitors on human eosinophil functions. Brit J Pharmacol 114: 821–831, 1995). Briefly, total granulocytes were first purified from blood (anticoagulated with 0.3% w/v sodium citrate) by dextran sedimentation, centrifugation on Ficoll Paque and hypotonic lysis of remaining red blood cells. For the further purification of the eosinophil fraction the magnetic cell separation (MACS) system from Miltenyi Biotec (Bergisch-Gladbach, Germany) was applied. Eosinophils were separated from neutrophils by negative selection using anti-CD16 microbeads in a two-step protocol using D- and BS-(formerly called $B_2$-) separation columns. By this method human eosinophils with a purity of >99% and a viability of >97% were obtained.

The chemiluminescence (CL) assay was essentially performed as described (Hatzelmann et al., 1995). Briefly, measurements were performed in a "CL-buffer" (140 mM NaCl, 5 mM KCl, 1 mM $MgCl_2$, 10 mM HEPES, pH 7.4) containing 1 mM $CaCl_2$, 1 mg/ml glucose, 0.05% (w/v) BSA, 10 μM luminol and 4 μM microperoxidase (all values correspond to final concentrations in the assays) in a total volume of 0.5 ml at a cell concentration of $10^6$ cells/ml. Aliquots (0.4 ml) of the cell suspension (containing luminol and microperoxidase) were preincubated for 5 min at 37° C. in the absence or presence of inhibitors (0.05 ml). Stock solutions of the inhibitors (10 mM) were prepared in DMSO and diluted 1:100 (v/v) in CL-buffer; subsequent dilutions were made in 1% DMSO/CL-buffer to achieve the final drug concentrations in the assays at a DMSO concentration of 0.1% (v/v) which by itself only weakly affected the CL response. As a further addition (0.01 ml) during the preincubation of the cells salbutamol (100 nM final concentration, which by itself hardly affected the CL response) was included as additional cAMP trigger. After preincubation, the assays were transferred into a "Multibiolumat LB 9505C" from Berthold (Wildbad, Germany) and stimulated by the addition of 0.05 ml C5a (dissolved in CL-buffer; 100 nM final concentration). CL was continuously recorded for 1 min (C5a) and the AUC (area under the curve) calculated. Inhibition of CL by the compounds under these conditions is given as $-\log IC_{30}$ (mol/l).

The inhibition of CL by the compounds according to the invention [as $-\log IC_{30}$ (mol/l)] follow from the Table A below, in which the numbers of the compounds correspond to the number of the examples.

TABLE A

| Compound | Inhibition of PDE4 activity [-logIC$_{50}$ (mol/l)] | β2-Adrenoceptor agonistic affinity [-logEC$_{50}$ (mol/l)] | Inhibition of C5a-stimulated chemiluminescence [-logIC$_{30}$ (mol/l)] |
|---|---|---|---|
| 1 | 6.97 | 7.89 | 5.52 |
| 2 | 7.33 | 6.86 | <5 |
| 3 | 7.47 | 6.77 | 6.52 |
| 5 | 8.31 | | 6.70 |
| 6 | 7.69 | 7.60 | 6.00 |
| 8 | 8.18 | | 6.40 |
| 11 | 7.59 | 8.11 | 6.22 |
| 12 | 7.65 | 8.61 | 5.92 |
| 13 | 7.80 | 6.91 | 6.52 |
| 14 | 7.43 | 7.24 | 5.30 |
| 20 | 10.17 | 8.64 | 7.10 |
| 21 | 10.03 | | 6.52 |
| 22 | 9.79 | | 6.70 |
| 25 | 10.62 | | 6.10 |
| 27 | 11.20 | | 6.40 |
| 30 | 10.67 | | 6.70 |
| 32 | 11.40 | | 6.64 |
| 33 | 10.07 | | 6.30. |

What is claimed is:

1. A compounds of formula I:

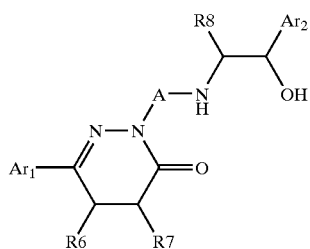

in which

Ar₁ represents a phenyl radical of formula (Ia) substituted by R1 and R2 or a dihydrobenzofuranyl radical of formula (Ib) substituted by R3, R4 and R5:

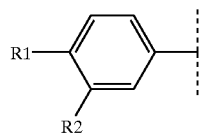

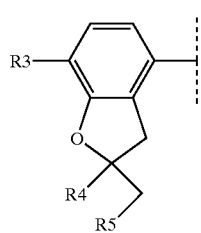

wherein

R1 is hydroxyl, halogen, 1–4C-alkoxy or 1–4C-alkoxy which is completely or predominantly substituted by fluorine, R2 is hydroxyl, halogen, 1–8C-alkoxy, 3–7C-cycloalkoxy, 3–7C-cycloalkylmethoxy, or 1–4C-alkoxy which is completely or predominantly substituted by fluorine, R3 is 1–4C-alkoxy, 3–5C-cycloalkoxy, 3–5C-cycloalkylmethoxy, or 1–4C-alkoxy which is completely or predominantly substituted by fluorine, R4 is 1–4C-alkyl and R5 is hydrogen or 1–4C-alkyl, or wherein R4 and R5 together and with inclusion of the two carbon atoms, to which they are bonded, form a spiro-linked 5-, 6- or 7-membered hydrocarbon ring, optionally interrupted by an oxygen or sulphur atom, R6 and R7 represent independently from one another hydrogen or 14C-alkyl, or R6 and R7 together and with inclusion of the two carbon atoms, to which they are bonded, form a group selected from:

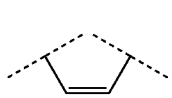 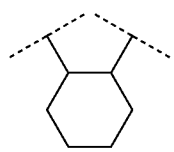 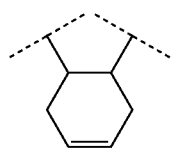

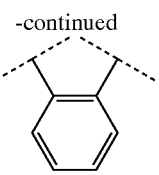

A represents —$C_mH_{2m}$—Y—X—$C_nH_{2n}$— or —Y—X—$C_mH_{2m}$-Z-$C_nH_{2n}$—, wherein X represents a bond, —O— (oxygen), —S— (sulfur), —NH—, —C(O)—, —S(O)₂—, —C(O)—NH—, —NH—C(O)—, —C(S)—NH—, —NH—C(S)—, —NH—C(O)—NH— or —NH—C(S)—NH—, Y represents a bond, phenylene, 4–8C-cycloalkylene or azacycloalkylene, Z represents —O—, —S—, —S(O)₂—, —NH—C(O)—, —C(O)—NH—, —NH—C(S)— or —C(S)—NH—, m is an integer from 0 to 4, n is an integer from 1 to 4, R8 is hydrogen or 1–4C-alkyl, Ar₂ represents a 8-hydroxy-1H-quinolin-2-on-5-yl radical or a phenyl radical substituted by R9, R10 and R11, wherein R9 is hydrogen, halogen, hydroxyl, amino, ureido [—NH—C(O)—NH₂], formylamino [—NH—C(O)H], 1-4C-alkylcarbonylamino, di-1-4C-alkylaminocarbonyloxy, tolylcarbonyloxy [—OC(O)—C₆H₄—CH₃], hydroxymethyl, 1-4C-alkylcarbonyloxy, 1-4C-alkyl, 1-4C-alkoxy, 1-4C-alkylsulfonylamino, 1-4C-alkylsulfonylmethyl or 1-4C-alkoxy-1-4C-alkyl, R10 is hydrogen, halogen, hydroxyl, cyano, trifluoromethyl, tolylcarbonyloxy [—O—C(O)—C₆H₄—CH₃], hydroxymethyl or 1-4C-alkylcarbonyloxy, R11 is hydrogen or halogen, or a salt thereof.

2. A compounds of formula I according to claim 1 in which

Ar₁ represents a phenyl radical of formula (Ia) substituted by R1 and R2 or a dihydrobenzofuranyl radical of formula (Ib) substituted by R3, R4 and R5

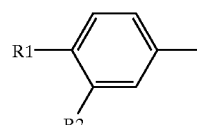

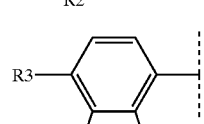

wherein

R1 is 1–4C-alkoxy or 1–4C-alkoxy which is completely or predominantly substituted by fluorine, R2 is 1–4C-alkoxy, 3–5C-cycloalkoxy, 3–5C-cycloalkylmethoxy, or 1–4C-alkoxy which is completely or predominantly substituted by fluorine, R3 is 1–4C-alkoxy, 3–5C-cycloalkoxy, 3–5C-cycloalkylmethoxy, or 1–4C-alkoxy which is completely or predominantly substituted by fluorine,
R4 is 1–4C-alkyl and
R5 is hydrogen or 1–4C-alkyl,
or wherein
R4 and R5 together and with inclusion of the two carbon atoms, to which they are bonded, form a spiro-linked cyclopentane, cyclohexane, tetrahydrofuran or tetrahydropyran ring,
R6 and R7 represent independently from one another hydrogen or 1–4C-alkyl, or R6 and R7 together and with inclusion of the two carbon atoms, to which they are bonded, form a group selected from:

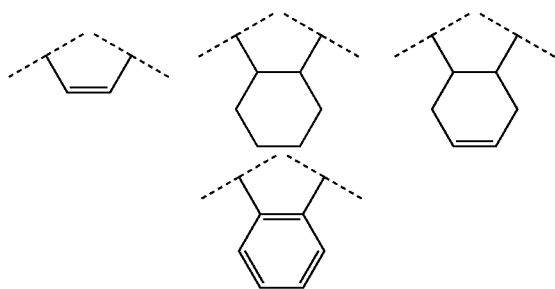

and A either represents —$C_mH_{2m}$—Y—X—$C_nH_{2n}$—, wherein either
X represents a bond,
Y represents a bond,
m is an integer from 1 to 4, and
n is an integer from 1 to 4,
or
X represents a bond, —O—, —S—, —C(O)—, —S(O)$_2$—, —C(O)—NH— or —C(S)—NH—,
Y represents 1,4-phenylene, 1,3-phenylene, 1,4-cyclohexylene, 1,3-cyclohexylene or 1,3-cyclopentylene,
m is an integer from 0 to 4, and
n is an integer from 1 to 4,
or
X represents a bond, —C(O)—, —S(O)$_2$—, —C(O)—NH— or —C(S)—NH—,
Y represents 4,1-piperidinylene,
m is 0, and
n is an integer from 1 to 4,
or
X represents a bond, —C(O)—, —S(O)$_2$—, —C(O)—NH— or —C(S)—NH—,
Y represents 1,4-piperazinylene,
m is an integer from 1 to 4, and
n is an integer from 1 to 4,
or
A represents —Y—X—$C_mH_{2m}$-Z-$C_nH_{2n}$—, wherein
X represents a bond, —C(O)—, —S(O)$_2$—, —C(O)—NH— or —C(S)—NH—,
Y represents 4,1-piperidinylene,
Z represents a bond, —O—, —S—, —S(O)$_2$— or —C(O)—NH—,
m is an integer from 1 to 4, and
n is an integer from 1 to 4,
or
X represents a bond, —O—, —S—, —C(O)—, —S(O)$_2$—, —C(O)—NH— or —C(S)—NH—,
Y represents 1,4-phenylene, 1,3-phenylene, 1,4-cyclohexylene, 1,3-cyclohexylene or 1,3-cyclopentylene, Z represents a bond, —O—, —S—, —S(O)$_2$— or —C(O)—NH—,
m is an integer from 1 to 4, and
n is an integer from 1 to 4,
R8 is hydrogen, methyl or ethyl,
Ar$_2$ represents a 8-hydroxy-1H-quinolin-2-on-5-yl radical or a phenyl radical substituted by R9, R10 and R11,
wherein
R9 is hydrogen, halogen, hydroxyl, amino, ureido [—NH—C(O)—NH$_2$], formylamino [—NH—C(O)H], 1–4C-alkylcarbonylamino, di-1–4C-alkylaminocarbonyloxy, tolylcarbonyloxy [—O—C(O)—$C_6H_4$—$CH_3$], hydroxymethyl, 1–4C-alkylcarbonyloxy, 1–4C-alkyl, 1–4C-alkoxy, 1–4C-alkylsulfonylamino, 1–4C-alkylsulfonylmethyl or 1–4C-alkoxy-1–4C-alkyl,
R10 is hydrogen, halogen, hydroxyl, cyano, trifluoromethyl, tolylcarbonyloxy [—O—C(O)—$C_6H_4$—$CH_3$], hydroxymethyl or 1–4C-alkylcarbonyloxy,
R11 is hydrogen or halogen,
or a salt thereof.

3. A compounds of formula I according to claim 1 in which

Ar$_1$ represents a phenyl radical of formula (Ia) substituted by R1 and R2 or a dihydrobenzofuranyl radical of formula (Ib) substituted by R3, R4 and R5:

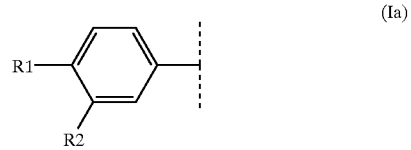

(Ia)

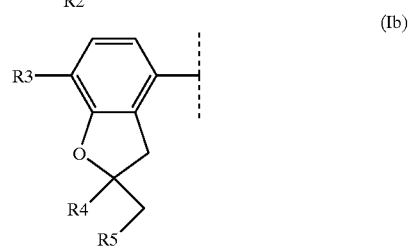

(Ib)

wherein
R1 is 1–2C-alkoxy or 1–2C-alkoxy which is completely or predominantly substituted by fluorine,
R2 is 1–2C-alkoxy, 3–5C-cycloalkoxy, 3–5C-cycloalkylmethoxy, or 1–2C-alkoxy which is completely or predominantly substituted by fluorine,
R3 is 1–2C-alkoxy or 1–2C-alkoxy which is completely or predominantly substituted by fluorine,
R4 is methyl and
R5 is hydrogen,
or wherein
R4 and R5 together and with inclusion of the two carbon atoms, to which they are bonded, form a spiro-linked cyclopentane or cyclohexane ring,
R6 and R7 together and with inclusion of the two carbon atoms, to which they are bonded, form a group selected from:

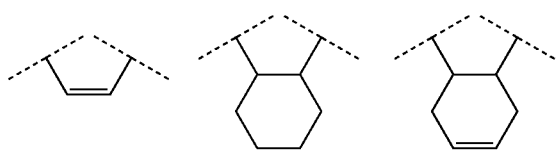

and A either represents —$C_mH_{2m}$—Y—X—$C_nH_{2n}$—, wherein either
X represents a bond,
Y represents a bond,
m is an integer from 1 to 4, and
n is an integer from 1 to 4,
or
X represents a bond, —O— or —C(O)—NH—,
Y represents 1,4-phenylene or 1,4-cyclohexylene,
m is an integer from 0 to 4, and
n is an integer from 1 to 4,
or
X represents a bond, —C(O)—, —S(O)$_2$— or —C(S)—NH—,
Y represents 4,1-piperidinylene,
m is 0, and
n is an integer from 1 to 4,
or
A represents —Y—X—$C_mH_{2m}$-Z-$C_nH_{2n}$—, wherein either
X represents a bond or —C(O)—,
Y represents 4,1-piperidinylene,
Z represents a bond, —S— or —S(O)$_2$—,
m is an integer from 1 to 4,
n is an integer from 1 to 4,
or
X represents a bond, —O— or —C(O)—NH—,
Y represents 1,4-phenylene or 1,4-cyclohexylene,
Z represents a bond,
m is an integer from 1 to 4, and
n is an integer from 1 to 4,
R8 is hydrogen,
Ar$_2$ represents a 8-hydroxy-1H-quinolin-2-on-5-yl radical or a phenyl radical substituted by R9, R10 and R11,
wherein
R9 is hydrogen, hydroxyl or amino,
R10 is hydrogen, halogen, cyano, trifluoromethyl or hydroxymethyl,
R11 is hydrogen or halogen,
or a salt thereof.

4. A compounds of formula I according to claim 1 in which
Ar$_1$ represents a phenyl radical of formula (Ia) substituted by R1 and R2 or a dihydrobenzofuranyl radical of formula (Ib) substituted by R3, R4 and R5

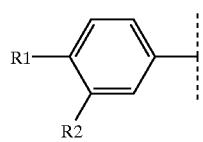
(Ia)

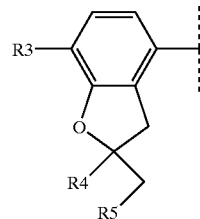
(Ib)

wherein
R1 is methoxy or ethoxy,
R2 is methoxy or ethoxy,
R3 is methoxy,
R4 and R5 together and with inclusion of the two carbon atoms, to which they are bonded, form a spiro-linked cyclopentane ring,
R6 and R7 together and with inclusion of the two carbon atoms, to which they are bonded, form a group selected from:

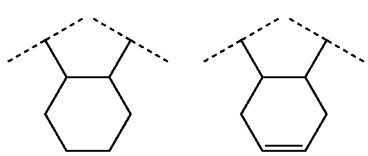

and A either represents —$C_mH_{2m}$—Y—X—$C_nH_{2n}$—, wherein either
X represents a bond,
Y represents a bond,
m is an integer from 1 to 4, and
n is an integer from 1 to 4,
or
X represents a bond, —O— or —C(O)—NH—,
Y represents 1,4-phenylene,
m is an integer from 0 to 1, and
n is an integer from 1 to 4,
or
X represents a bond, —C(O)—, —S(O)$_2$— or —C(S)—NH—,
Y represents 4,1-piperidinylene,
m is 0, and
n is an integer from 1 to 4,
or A represents —Y—X—$C_mH_{2m}$-Z-$C_nH_{2n}$—, wherein
X represents a bond or —C(O)—,
Y represents 4,1-piperidinylene,
Z represents a bond, —S— or —S(O)$_2$—,
m is 2 or 3, and
n is 2 or 3,
R8 is hydrogen,
Ar$_2$ is phenyl, 4-amino-3-chloro-5-cyanophenyl, 4-amino-3-chloro-5-trifluoromethylphenyl, 4-hydroxy-3-hydroxymethylphenyl, 4-amino-3-cyanophenyl or 4-amino-3,5-dichlorophenyl,
or a salt thereof.

5. A compounds of formula I according to claim 1 in which
Ar$_1$ represents a phenyl radical of formula (Ia) substituted by R1 and R2 or a dihydrobenzofuranyl radical of formula (Ib) substituted by R3, R4 and R5

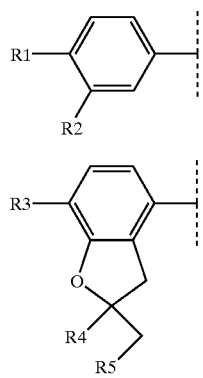

(Ia)

(Ib)

wherein

R1 is hydroxyl, halogen, 1–4C-alkoxy or 1–4C-alkoxy which is completely or predominantly substituted by fluorine, R2 is hydroxyl, halogen, 1–8C-alkoxy, 3–7C-cycloalkoxy, 3–7C-cycloalkylmethoxy, or 1–4C-alkoxy which is completely or predominantly substituted by fluorine, R3 is 1–4C-alkoxy, 3–5C-cycloalkoxy, 3–5C-cycloalkylmethoxy, or 1–4C-alkoxy which is completely or predominantly substituted by fluorine, R4 is 1–4C-alkyl and R5 is hydrogen or 1–4C-alkyl, or wherein R4 and R5 together and with inclusion of the two carbon atoms, to which they are bonded, form a spiro-linked 5-, 6- or 7-membered hydrocarbon ring, optionally interrupted by an oxygen or sulphur atom, R6 and R7 represent independently from one another hydrogen or 1–4C-alkyl, or R6 and R7 together and with inclusion of the two carbon atoms, to which they are bonded, form a group selected from:

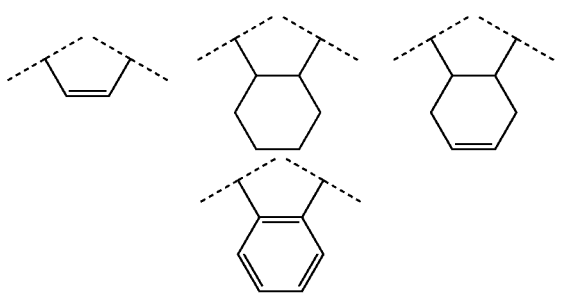

A represents —(CH$_2$)$_m$—Y—X—(CH$_2$)$_n$—, wherein

X represents a bond, —O— (oxygen), —S— (sulfur), —NH—, —C(O)—, —C(O)—NH— or —NH—C(O)—NH—, Y represents a bond, phenylene, 4–8C-cycloalkylene or azacycloalkylene, m is an integer from 0 to 4, n is an integer from 1 to 4, R8 is hydrogen or 1–4C-alkyl, Ar$_2$ represents a 8-hydroxy-1H-quinolin-2-on-5-yl radical or a phenyl radical substituted by R9, R10 and R11, wherein R9 is hydrogen, halogen, hydroxyl, amino, ureido [—NH—C(O)—NH$_2$], formylamino [—NH—C(O)H], 1–4C-alkylcarbonylamino, di-1–4C-alkylaminocarbonyloxy, tolylcarbonyloxy [—O—C(O)—C$_6$H$_4$—CH$_3$], hydroxymethyl, 1–4C-alkylcarbonyloxy, 1–4C-alkyl, 1–4C-alkoxy, 1–4C-alkylsulfonylamino, 1–4C-alkylsulfonylmethyl or 1–4C-alkoxy-1–4C-alkyl, R10 is hydrogen, halogen, hydroxyl, cyano, trifluoromethyl, tolylcarbonyloxy [—O—C(O)—C$_6$H$_4$—CH$_3$], hydroxymethyl or 1–4C-alkylcarbonyloxy, R11 is hydrogen or halogen, or a salt thereof.

6. A compounds of formula I according to claim 1 in which

Ar$_1$ represents a phenyl radical of formula (Ia) substituted by R1 and R2 or a dihydrobenzofuranyl radical of formula (Ib) substituted by R3, R4 and R5

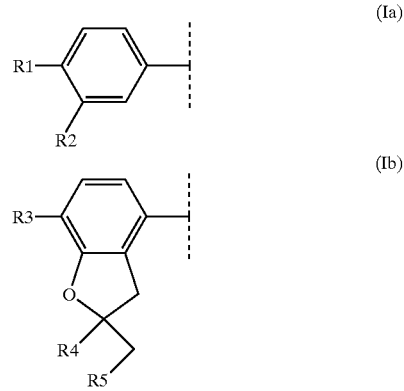

wherein

R1 is 1–2C-alkoxy or 1–2C-alkoxy which is completely or predominantly substituted by fluorine, R2 is 1–2C-alkoxy, 3–5C-cycloalkoxy, 3–5C-cycloalkylmethoxy, or 1–2C-alkoxy which is completely or predominantly substituted by fluorine, R3 is 1–2C-alkoxy or 1–2C-alkoxy which is completely or predominantly substituted by fluorine, R4 is methyl and R5 is hydrogen, or wherein R4 and R5 together and with inclusion of the two carbon atoms, to which they are bonded, form a spiro-linked cyclopentane or cyclohexane ring, R6 and R7 together and with inclusion of the two carbon atoms, to which they are bonded, form a group selected from:

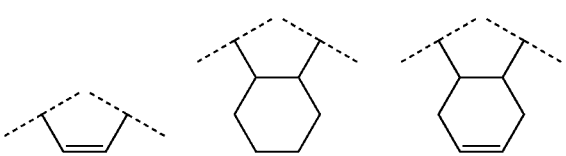

A represents —(CH$_2$)$_m$—Y—X—(CH$_2$)$_n$—, wherein

X represents a bond or —C(O)—,

Y represents a bond, 1,4-phenylene, 1,4-cyclohexylene or 4,1-piperidinylene, m is an integer from 0 to 4, n is an integer from 1 to 4, R8 is hydrogen,
Ar₂ represents a 8-hydroxy-1H-quinolin-2-on-5-yl radical or a phenyl radical substituted by R9, R10 and R11, wherein
R9 is hydrogen, hydroxyl or amino,
R10 is hydrogen, halogen, cyano, trifluoromethyl or hydroxymethyl,
R11 is hydrogen or halogen,
or a salt thereof.

7. A compounds of formula I according to claim 1 in which
Ar₁ represents a phenyl radical of formula (Ia) substituted by R1 and R2 or a dihydrobenzofuranyl radical of formula (Ib) substituted by R3, R4 and R5

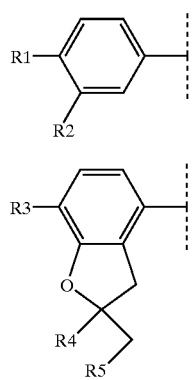

wherein
R1 is methoxy, ethoxy or difluoromethoxy,
R2 is methoxy or ethoxy,
R3 is methoxy,
R4 and R5 together and with inclusion of the two carbon atoms, to which they are bonded, form a spiro-linked cyclopentane ring, R6 and R7 together and with inclusion of the two carbon atoms, to which they are bonded, form a group selected from:

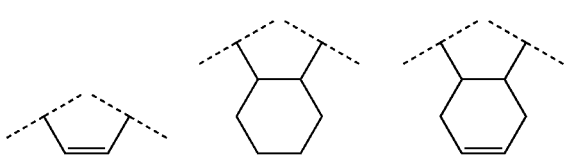

A represents —(CH₂)$_m$—Y—X—(CH₂)$_n$—, wherein
X represents a bond,
Y represents a bond or 1,4-phenylene,
m is an integer from 0 to 4,
n is an integer from 1 to 4,
R8 is hydrogen,
Ar₂ is phenyl, 4-amino-3-chloro-5-cyanophenyl, 4-amino-3-chloro-5-trifluoromethyl, 4-hydroxy-3-hydroxymethylphenyl, 4-amino-3-cyanophenyl or 4-amino-3,5-dichlorphenyl,
or a salt thereof.

8. A pharmaceutically composition comprising one or more compounds of formula I according to claim 1 or a pharmaceutically acceptable salt thereof, together with pharmaceutically acceptable auxiliaries and/or carrier materials.

9. A method of treating an airway disorder in a patient comprising administering to a patient in need thereof a therapeutically effective amount of one or more compounds of formula I according to claim 1 or a pharmaceutically acceptable salt thereof, wherein the disease or disorder is selected from the group consisting of bronchial asthma, COPD and allergic rhinitis.

* * * * *

UNITED STATES PATENT AND TRADEMARK OFFICE
CERTIFICATE OF CORRECTION

PATENT NO.     : 6,933,296 B2
DATED          : August 23, 2005
INVENTOR(S)    : Sterk et al.

It is certified that error appears in the above-identified patent and that said Letters Patent is hereby corrected as shown below:

Column 49,
Line 2, please delete "A compounds" and replace with -- A compound --.
Line 55, please delete "sulphur" and replace with -- sulfur --.
Line 57, please delete "14C-alkyl" and replace with -- 1-4C-alkyl --.

Column 50,
Lines 28-29, please delete "[-OC(O)-$C_6H_4$-$CH_3$]" and replace with
-- [-OC-(O)-$C_6H_4$-$CH_3$] --.
Line 39, please delete "A compounds" and replace with -- A compound --.

Column 52,
Line 26, please delete "A compounds" and replace with -- A compound --.

Column 53,
Line 34, please delete "Z represents a bond, -S- or -$S(O)_2$-," and replace with
-- "Z represents a bond, -O-, -S- or $S(O)_2$-, --.
Line 55, please delete "A compounds" and replace with -- A compound --.

Column 54,
Line 62, please delete "A compounds" and replace with -- A compound --.

Column 56,
Line 13, please delete "A compounds" and replace with -- A compound --.

Column 57,
Line 10, please delete "A compounds" and replace with -- A compound --.

Column 58,
Line 22, please delete "4-amino-3,5-dichlorphenyl" and replace with
-- 4-amino-3,5-dichlorophenyl --.

UNITED STATES PATENT AND TRADEMARK OFFICE
CERTIFICATE OF CORRECTION

PATENT NO.   : 6,933,296 B2
DATED        : August 23, 2005
INVENTOR(S)  : Sterk et al.

It is certified that error appears in the above-identified patent and that said Letters Patent is hereby corrected as shown below:

Column 58 (cont'd),
Line 25, please delete "A pharmaceutically" and replace with -- A pharmaceutical --.

Signed and Sealed this

Eleventh Day of October, 2005

JON W. DUDAS
*Director of the United States Patent and Trademark Office*